United States Patent [19]
Kent et al.

[11] Patent Number: 6,040,133
[45] Date of Patent: Mar. 21, 2000

[54] D-ENZYME COMPOSITIONS AND METHODS OF THEIR USE

[75] Inventors: Stephen Brian Henry Kent; Saskia Charlotte Florence Milton; Raymond Cecil deLisle Milton, all of La Jolla, Calif.

[73] Assignee: The Scripps Research Institute, La Jolla, Calif.

[21] Appl. No.: 08/651,144

[22] Filed: May 22, 1996

Related U.S. Application Data

[60] Division of application No. 08/343,585, Dec. 2, 1994, which is a continuation-in-part of application No. 07/894,817, Jun. 8, 1992, abandoned.

[51] Int. Cl.[7] .............. C12Q 1/00; C12Q 1/37; C12Q 1/34; C12Q 1/44

[52] U.S. Cl. .................. 435/4; 435/23; 435/24; 435/28; 435/25; 435/19; 435/18

[58] Field of Search ................. 435/4, 23, 24, 435/28, 25, 19, 18

[56] References Cited

U.S. PATENT DOCUMENTS 5,098,836  3/1992  Stahl et al. ............................ 435/4
5,157,019  10/1992  Glover et al. ........................ 435/4

*Primary Examiner*—Louise N. Leary
*Attorney, Agent, or Firm*—Donald G. Lewis

[57] ABSTRACT

D-enzyme compositions are described comprising an amino acid residue sequence that defines an polypeptide able to catalyze an enzymatic reaction. The D-enzyme has an amino acid residue sequence consisting essentially of D-amino acids.

2 Claims, 13 Drawing Sheets

Boc-NHCHRCO ∼∼∼ RESIN

│    1. DEPROTECT: $CF_3COOH$
    │
    │    2. DMF FLOW WASH
    ▼

$CF_3COO^-\cdot {}^+NH_3$-CHRCO ∼∼∼ RESIN

│    1. COUPLE: Boc-AA + HBTU
    │                       + DIEA
    │    2. DMF FLOW WASH
    ▼

Boc-AA-NHCHRCO ∼∼∼ RESIN

FIG. 5

|  | L | | D | |
|---|---|---|---|---|
|  | mg | % | mg | % |
| HIV-1 PR (1-50, Gly α -COSH) | 80.1 | 5.0 | 79.0 | 4.4 |
| BROMOACETYL (53-99) HIV-1 PR | 93.6 | 7.6 | 124.6 | 9.3 |
| [(NHCH$_2$COSCH$_2$CO)$^{51-52}$] HIV-1 PR | 75.8 | 67.4 | 80.8 | 44.0 |
| FOLDED [Aba$^{67,95}$, (CO-S)$^{51-52}$]$_2$ HIV-1 PR | 47.4* | 53.3 | 48.2* | 60.0 |
| OVERALL YIELD |  | 3.0 |  | 2.5 |

FIG. 7

*YIELD EXTRAPOLATED FROM A FOLDING EXPERIMENT WITH A SMALL AMOUNT OF MATERIAL

D-ENZYME COMPOSITIONS AND METHODS OF THEIR USE

This is a divisional, of application Ser. No. 08/343,585, filed Dec. 2, 1994, which is a continuation-in-part of application Ser. No. 07/894,817, filed Jun. 5, 1992, now abandoned whose disclosures are incorporated herein by reference.

TECHNICAL FIELD

The present invention relates to proteins incorporating D-amino acid residues. More particularly, the present invention relates to enzymically active proteins consisting essential of D-amino acids and methods for using such proteins.

BACKGROUND

The biosphere is inherently chiral; each class of biological macromolecules is made up of monomer molecules of uniform chirality (Mason, Chirality3:223, 1991) and the biochemical interactions of biological macromolecules are inherently chiral.

Enzymes, for example, invariably act only on one enantiomer of a chiral substrate, or generate only one diastereomer from a prochiral substrate. Fersht, in "Enzyme Structure and Mechanism", W. H. Freeman and Company, San Francisco, 1977, pp. 75–81. This specificity can be related to the chiral structure of the enzyme molecule, including the three-dimensional folding of the polypeptide backbone and the orientation of the amino acid side chains in the folded protein molecule. Fersht, supra. To date only L-enzymes have been described in nature; this leaves the description of D-enzymes and their properties, which include folded structure, enzymatic activity, and chiral specificity, as unexplored questions.

Recently, Zawadzke et al., J. Am. Chem. Soc., 114:4002–4003, 1992, described the preparation of a small 45 amino acid residue polypeptide (D-rubrodoxin) using D-amino acids. L-rubrodoxin is found in clostridia and is the simplest iron-sulfur protein. It is believed to function in electron transport. However, it lacks an demonstrated enzymic activity.

Prior to the present invention, the largest L-protein known to be chemically synthesized in a conventional step-wise fashion is Preprogonadotropin Release Hormone (PreproGnRH). PreproGnRH has 93 amino acid residues. (Milton et al., Biochemistry, (1992) 31: 8800.) PreproGnRH inhibits prolactin release.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

The property of optical activity is due to molecular asymmetry about carbon atoms that are linked to four different atoms or molecules. Where there is only one asymmetric carbon atom, or chiral center as it is sometimes called, there are two possible stereoisomers. Where there are n asymmetric carbons or chiral centers, the number of potential stereoisomers increases to $2^n$. Thus, a molecule with three chiral centers would have eight possible stereoisomers.

While the structural differences between stereoisomers are subtle and of little consequence in ordinary chemical reactions, they may be profound where biological systems are concerned, i.e., if the compounds are utilized in enzyme-catalyzed reactions. Thus, the L-amino acids are readily metabolized in humans but the corresponding D-analogs are not, and only D-glucose can be phosphorylated and processed into glycogen or degraded by the glycolytic and oxidative pathways of intermediary metabolism. Similarly, beta blockers, pheromones, prostaglandins, steroids, flavoring and fragrance agents, pharmaceuticals, pesticides, herbicides, and many other compounds exhibit critical stereospecificity. In the field of pesticides, Tessier [Chemistry and Industry, Mar. 19, 1984, p. 199] has shown that only two of the eight stereoisomers of deltamethrin, a pyrethroid insecticide, have any biological activity. The same statement concerning the concentration of bioactivity in a single isomer can be made about many other pesticides, including the phenoxypropionates and halopropionate derivatives, each containing one chiral center and existing in the form of two optical isomers.

Stereochemical purity is of equal importance in the field of pharmaceuticals, where 12 of the 20 most prescribed drugs exhibit chirality. A case in point is provided by naproxen, or (+)-S-2-(6-methoxy-2-naphthyl)-propionic acid, which is one of the two most important members of a class of 2-aryl-propionic acids with non-steroidal anti-inflammatory activity used, for instance, in the management of arthritis. In this case, the S(+) enantiomer of the drug is known to be 28 times more therapeutically potent that its R(−) counterpart. Still another example of chiral pharmaceuticals is provided by the family of beta-blockers, the L-form of propranolol is known to be 100 times more potent that the D-enantiomer.

Synthesis of chiral compounds by standard organic synthetic techniques generally leads to a racemic mixture which, in the aggregate, may have a relatively low specific bioactivity since certain of the stereoisomers in the mixture are likely to be biologically or functionally inactive. As a result, larger quantities of the material must be used to obtain an effective dose, and manufacturing costs are increased due to the co-production of stereochemically "incorrect" and hence, inactive ingredients.

In some instances, certain isomers may actually be deleterious rather than simply inert. For example, the D-enantiomer of thalidomide was a safe and effective sedative when prescribed for the control of morning sickness during pregnancy. However, its L-thalidomide counterpart was discovered to be a potent mutagen.

Methods are available for stereoselective synthesis that generally involve chemical synthesis and isolation steps that are lengthy, complex and costly. Moreover, a synthetic scheme capable of producing one specific enantiomer cannot be applied in a general way to obtain other optically active compounds. What is needed is a generalized approach to the resolution of racemic mixtures produced by ordinary chemical reactions, and a number of approaches have been used.

A widely used approach has been the selective precipitation of desired compounds from racemic mixtures. See, for example, Yoshioka et al. [U.S. Pat. No. 3,879,451], Paven et al. [U.S. Pat. No. 4,257,976], Halmos [U.S. Pat. No. 4,151,198], and Kameswaran [U.S. Pat. No. 4,454,344].

The above procedures successfully resolved racemic mixtures because treatment of the mixtures with optically pure reagents produced diastereomers which, unlike the initial racemic compounds, have different physical properties. Thus, fractional crystallization or other physical means may be employed to separate diastereomeric compounds.

Separation of diastereomers can also be carried out by chromatography. For example, Pollock et al. [J. Gas Chromatogr. 3: 174 (1965)] have resolved diastereomeric amino acids by gas chromatography. Mikes et al. [J. Chromatogr. 112:205 (1976)] have used liquid chromatography to resolve diastereomeric dipeptides. In most cases, the optically pure reagents have been in the stationary phase during chromatographic separation, but they may also be used in elutants. Hare et al. [U.S. Pat. No. 4,290,893] have used liquid chromatography to resolve racemic mixtures that were treated with aqueous elutants containing optically pure reagents and metal cations; resolution occurred because the resulting diastereomeric complexes had different partition coefficients in the chromatographic system.

All of the methods described to this point have relied upon the availability of suitable optically pure reagents, but such reagents are often not available or else their use is prohibitively expensive. In an alternative approach, enzymatic resolution techniques have been developed. Many different classes of enzymes have been used for the resolution of stereoisomers on a preparative scale, including hydrolases (especially the lipases and esterases such as chymotrypsin), lyases, and oxidoreductases (e.g., amino acid oxidases and alcohol reductases). Generally speaking, enzymes for use in resolutions should ideally exhibit broad substrate specificity, so that they will be capable of catalyzing reactions of a wide range of "unnatural" substrates, and a high degree of stereoselectivity for catalyzing the reaction of one isomer to the exclusion of others.

The hydrolases (e.g., lipases and esterases) are among the more attractive enzymes for use in resolutions, because they do not require expensive cofactors, and some of them exhibit reasonable tolerance to organic solvents. Additionally, chiral chemistry often involves alcohols, carboxylic acids, esters, amides, and amines with chiral carbons, and carboxyl hydrolases are preferred choices as stereoselective catalysts for reactions of such species. For instance, enzymatic treatment has been applied to the resolution of racemic mixtures of amino acid esters. Stauffer [U.S. Pat. No. 3,963,573] and Bauer [U.S. Pat No. 4,262,092].

Separation of reaction products from enzymes has been facilitated by attaching the enzyme to a solid support which could be removed by centrifugation or packed into a column through which the racemic mixtures were passed.

Enzymes have also been explored for the resolution of classes of compounds other than the amino acids discussed above. Immobilized lipase in principal resolves mixtures by enzymatic hydrolysis or transesterification. In the case of a biphasic hydrolysis reaction, the differing solubility properties of the acids and esters involved required the dispersion and agitation of mixtures containing the immobilized solid-phase enzyme, an aqueous buffer, and the water-immiscible organic phase containing solvent and reactant—a relatively inefficient process.

Enzymes have been applied to the resolution of optical isomers of insecticides. For instance, Mitsuda et al. [Eur. Patent Appl'n. Publ. No. 0 080 827 A2] contacted a racemic acetic acid ester with stereoselective esterases of microbial and animal origin in biphasic systems (i.e., aqueous/organic dispersion). In related work on optically purified pyrethroids, Mitsuda et al. [U.S. Pat. No. 4,607,013] employed microbial esterases. Klibanov et al. [U.S. Pat. No. 4,601,987] resolved racemic 2-halopropionic acids by means of lipase-catalyzed esterification reactions conducted in organic media.

Additional examples can also be provided of the state-of-the-art enzyme-mediated resolution as applied to the production of optically purified pharmaceuticals. Sih [U.S. Pat. No. 4,584,270] has disclosed enzymatic means for the production of optically pure (R)-4-amino-3-hydroxybutyric acid, a key intermediate in the preparation of L-carnitine.

Until recently only naturally occurring L enzymes could be described, and this left the presumed properties of D-enzymes, including their folded structures, enzymatic activity and chiral specificity, as unexplored questions. What was needed was sufficient progress in the chemical synthesis of proteins to make possible the total synthesis of the D-enantiomer of whole enzymes in sufficient quantity to form crystals and to perform other functions.

BRIEF SUMMARY OF THE INVENTION

A new type of enzyme designated a D-enzyme has been discovered that has ability to catalyze the reaction of a chiral substrate. Therefore, described herein is a D-enzyme comprising an amino acid residue sequence that defines an polypeptide able to catalyze an enzymatic reaction, wherein the amino acid residue sequence consists essentially of D-amino acids.

The enzymatic reaction can have achiral substrate specificity, or chiral substrate specificity. Preferred achiral substrate-specific D-enzymes are superoxide dismutase or carbonic anhydrase. A preferred chiral substrate-specific D-enzymes is HIV-1 protease.

The invention also contemplates a method of producing a chirally pure chemical comprising:

a) reacting in an aqueous admixture a first stereoisomer substrate with a D-enzyme that specifically converts the first stereoisomer substrate into a chiral reaction product, wherein the reaction occurs for a time period and under reaction conditions sufficient to form a reaction product; and b) isolating the chiral reaction product from the admixture, thereby forming the chirally pure chemical. In alternative embodiments, the aqueous admixture may comprise a racemic mixture or partial racemic mixture of a substrate having at least a first and a second stereoisomer or may comprise the first stereoisomer of the substrate alone.

A D-enzyme of this invention provides a wide variety of benefits and advantages which are apparent to the skilled practitioner. A D-enzyme provides a means to efficiently produce chirally pure chemicals for use as reagent grade industrial chemicals, and as pharmaceutically pure medicaments. In addition, a D-enzyme can be used in combination with its L-enzyme counterpart in co-crystallation admixtures to form racemic crystals for determining crystallographic structures using X-ray diffraction data. Furthermore, because of the inherent resistance of a D-enzyme from proteolysis by natural L-amino acid-specific proteases, therapeutically administered D-enzymes that have achiral substrate specificity can be utilized in place of the corresponding L-enzyme and enjoy prolonged half-lives in proteolytic environments such as the blood or digestive tract, thereby increasing the effectiveness of the therapeutic enzyme.

A D-enzyme of the present invention may also be employed for screening natural product libraries. More particularly, a D-enzyme may be employed to identify chiral inhibitors within a natural product library. In some instance, a natural product libarary may include a chiral inhibitor having activity with respect to D-enzyme but having no activity with respect to the corresponding L-enzyme. Synthesis of the enantiomer of the identified chiral inhibitor then results in the formation of an inhibitor of the corresponding L-enzyme.

BRIEF DESCRIPTION OF THE DRAWINGS

In the drawings forming a portion of this disclosure:

FIG. 1 illustrates the molecular weight characterization of the D- and L-enzyme enantiomers of the HIV-1 protease as described in Example 2 using reconstructed ion spray mass spectroscopy. The molecular weight is expressed in daltons, and is shown as a peak of the percent (%) of relative intensity of the measured spectra.

FIG. 2 illustrates the comparative enzyme activity of the HIV PR enzyme D- and L-enantiomers on D- and L-enantiomers of a chiral fluorogenic substrate as described in Example 3.

FIG. 5 illustrates a schematic representation of the optimized solid-phase chain assembly tactics employed in the synthesis of the functionalized peptide segments. Deprotection and coupling reactions are separated by a single flow wash step.

FIG. 7 illustrates the step reaction yields for the synthesis of the D- and L-[Aba$^{67,95}$ (CO—S)$^{51-52}$]$_2$HIV-1 protease analogs.

DETAILED DESCRIPTION OF THE INVENTION

A. Definitions

Amino Acid Residue

Figure 1A:
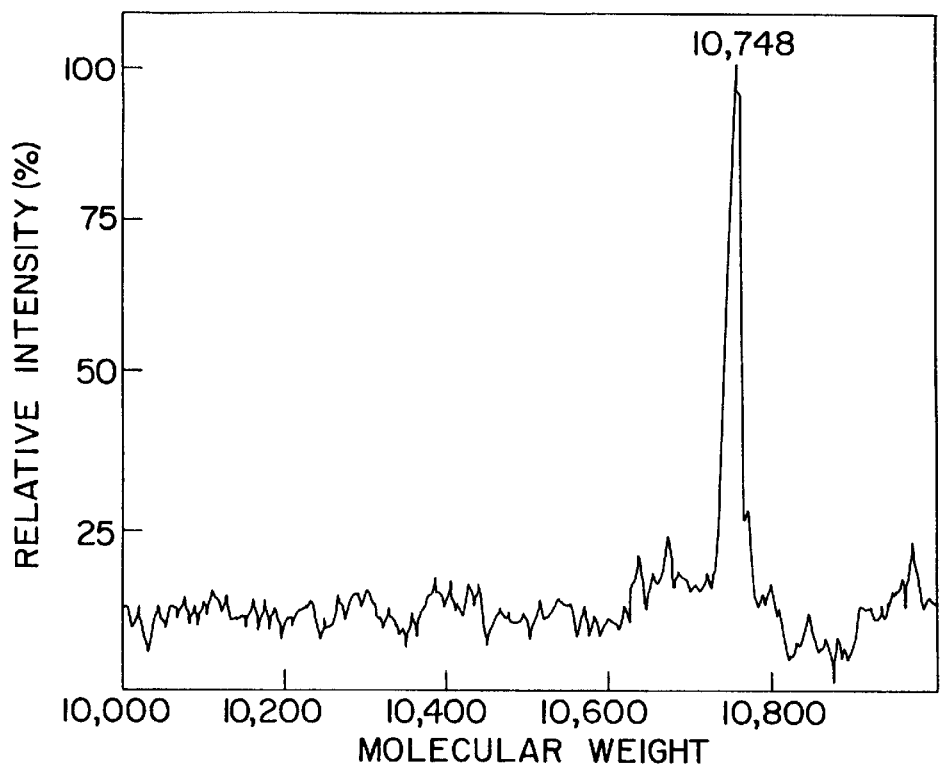
FIG. 1A illustrates molecular weight data obtained with the L-enzyme.

An amino acid formed upon chemical digestion (hydrolysis) of a polypeptide at its peptide linkages. The amino acid residues described herein are either in the "L" or "D" stereoisomeric form. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

The above symbols are employed for both L- and D-amino acid residues. The symbol Xaa is employed for any unknown or other amino acid residue. However, the symbol Xaa is frequently employed herein to designate L- or D-α-amino-n-butyric acid (aba), an isosteric replacement for Cys residues. It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 C.F.R. 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as NH$_2$ or acetyl or to a carboxy-terminal group such as COOH.

Racemic Mixture

A racemic mixture is used herein to refer to a mixture of at least a first and second stereoisomer in any proportions. In this context, the term "resolution" as used herein will refer to separation of a first racemic mixture into second and third mixtures wherein the proportions of the two stereoisomers in the second and third mixtures are different from that in the first racemic mixture, the proportion being greater in one and necessarily smaller in the other.

B. D-Enzyme Compositions

The present invention contemplates a D-enzyme comprising a molecule having an amino acid residue sequence that defines a polypeptide able to catalyze an enzymatic reaction. A D-enzyme has an amino acid residue sequence consisting essentially of D-amino acids.

The term "D-amino acid" does not indicate the direction of specific rotation of the molecule because it is well known that some amino acids are dextrorotatory whereas others are levorotatory. Rather, the terms denotes an absolute configuration by convention relative to the two possible stereoisomers of glyceraldehyde, D-glyceraldehyde and L-glyceraldehyde. See for example, Lehninger, in "Biochemistry", Worth Publishers, Inc., New York, 1970, pp. 76–78. Thus all stereoisomers that are stereochemically related to L-glyceraldehyde are designated L-, and those related to D-glyceraldehyde are designated D-, regardless of the direction of rotation of plane polarized light given by the isomer.

In the case of threonine and isoleucine, there are two stereochemical centers, i.e. the amino acid $C\alpha$ atoms and the $C\beta$ atoms. The D-threonine and D-isoleucine employed herein have stereochemistries at both the amino acid $C\alpha$ atoms opposite to the stereochemistry of L-threonine and L-isoleucine, i.e. D-threonine and D-isoleucine are complete mirror images of L-threonine and L-isoleucine, respectively.

Glycine is the only commonly occurring achiral amino acid. Accordingly, when a protein or enzyme is designated herein as a D- or L-protein or enzyme, it is meant that essentially all of the chiral amino acid residue comprising such protein or enzyme have the indicated chirality. The presence of achiral amino acid residues such as glycine within a protein or enzyme does not affect the designation of its chirality, as employed herein.

All chiral amino acids in protein described in nature are L-amino acids. Thus, proteins having only D-configuration chiral amino acids in their amino acid residue sequence (referred to as D-proteins) are unknown in nature.

In one embodiment, it is preferred that a D-enzyme have an amino acid residue sequence that corresponds, and preferably is identical to, the amino acid residue sequence of a known or "natural" enzyme. By "natural" is meant a sequence present on an enzyme isolated from nature without laboratory-mediated interventions directed at altering the enzyme's sequence. By "known" is meant either a natural enzyme or an enzyme that is the product of a sequence modifying process that alters the amino acid sequence to produce an enzyme with known enzymatic properties.

Many enzymes described in the scientific literature, too numerous to recite here, have been the subject of mutation of their natural amino acid residue sequence such that they no longer correspond in amino acid residue sequence to the sequence of a natural isolate, and yet still retain an enzymatic activity. Thus, in another embodiment, the invention contemplates D-enzymes having amino acid residue sequences that correspond to known enzymes.

A D-enzyme can have any of a variety of enzymatic activities as that activity is generally understood in biochemistry, meaning broadly the ability to reduce the activation energy of a reaction between one or more substrates to form one or more reaction products. For the purposes of this invention, it is useful to distinguish enzyme substrate specificities that are chiral and achiral.

Chiral specificity refers to the selectivity of an enzyme to catalyze the reaction of only one of two stereoisomers. Achiral specificity refers to the ability of the enzyme to react with a substrate that does not present a recognition-dependent asymmetric structure to the enzyme, i.e., enzyme-substrate recognition and catalysis is not dependent upon the presence of an asymmetric structure in the substrate binding region of the enzyme. Stated differently and in the context of the present invention relating to enantiomeric selectivity of a D-enzyme, an achiral substrate can be catalyzed by either a D- or L-enzyme because no asymmetric structures are present in the achiral substrate upon which enzyme binding and catalysis depends. In contrast, a chiral substrate can only be catalyzed by one or the other of a D- and L-enzyme pair because structural asymmetry of the substrate is involved in the binding and catalysis.

A further distinction can be made between chiral and achiral reaction products. For example, an achiral substrate may be converted into a chiral or an achiral reaction product. If an achiral substrate is converted to a chiral reaction product, the chirality of the reaction product will depend upon the chirality of the enzyme, i.e. an L- or D-enzyme. Similarly, a chiral substrate may be converted into a chiral or an achiral reaction product.

Many enzymes exhibit chiral specificity including the preferred and exemplary enzyme, HIV-1 protease. Similarly, there are many enzymes that exhibit achiral specificity, including superoxide dismutase and carbonic anhydrase.

Thus in one embodiment, the invention contemplates a D-enzyme having chiral specificity that converts (catalyzes the reaction of) a chiral substrate into a reaction product, but does not also convert the enantiomer (stereoisomer) of the chiral substrate. An example is the HIV-1 protease described herein which reacts only with the D-substrate and not the L-substrate.

In another embodiment, the invention contemplates a D-enzyme having achiral specificity wherein both the D-enzyme and the corresponding L-enzyme convert an achiral substrate into a reaction product. One example is the reaction catalyzed by superoxide dismutase upon superoxide radicals. Another example is the reaction catalyzed by carbonic anhydrase.

A D-enzyme of this invention can be any size (length of amino acids), and can be comprised of multiple subunits, as is well known for many characterized enzymes. A multiple subunit D-enzyme is comprised of all D-protein subunits. Protein subunits that make up an enzyme, or single protein subunit enzyme, range widely in size. Typical enzyme subunits are from 80 to 500 amino acid residues in length, although shorter and longer proteins are known, from about 50 amino acid residues to sizes in excess of 4000 amino acid residues.

The present invention in one embodiment generally concerns the use of D-enzymes in processes for the stereoselective synthesis or resolution of racemic mixtures of chiral organic acids, alcohols, amines, esters, amides, nitriles, hydantoins, and other chiral compounds in which an enzyme is used that is capable of stereoselectively catalyzing a reaction to convert one isomer of a chiral precursor to a chemically distinct optically active compound. Enzymes are well suited to the role of stereoselective catalysis inasmuch as they contain asymmetric, catalytically active sites in which the molecule being synthesized or undergoing resolution may bind. Because these enzyme active sites are themselves asymmetric, they permit two enantiomers of a given racemic substrate to be acted upon differentially, and they permit chiral products to be formed from achiral precursors.

For example, many enzymes exist that effectively catalyze the hydrolysis or condensation of ester and amide chemical functional groups. Many of these enzymes, but not all of them, belong to either one of two main classes of enzymes known as hydrolases or lyases as defined in the Recommendations of the Commission on Biochemical Nomenclature, Elsevier, Amsterdam, The Nomenclature and Classification of Enzymes (1972) p. 17–22. The term E.C. followed by a series of numbers as used herein, provides the identification of an enzyme pursuant to the Commission Recommendations.

Types of enzymes useful in the practice of the present invention include, but are not limited to, enzymes that catalyze the following categories of reactions:
    hydrolysis of esters to form acids and alcohols;
    formation of esters (i.e., esterifications) from acids and alcohols;
    transesterification, i.e., reaction of an ester with an alcohol or acid to form a different ester and a different alcohol or acid;
    transaminations (e.g., reaction between an alpha-keto acid and an amino acid);
    hydrolysis of amides (including peptide bonds and N-acyl compounds) to form acids and amines;
    formation of amides (including peptides) from acids and amines (or amino acids);
    hydrolysis of amino acid hydantoins to yield carbamoyl amino acids and amino acids; and
    hydrolysis of nitrites to form the corresponding amides and carboxylic acids (and in particular, hydrolysis of amino nitriles to amino amides and amino acids).

Specific examples of such enzymes include but are not limited to trypsin, chymotrypsin, thermolysin, rennin, pepsin, papain, carboxy peptidases, amino peptidases, penicillin and cephalosporin acylase, acetyl cholinesterase, cholesterol esterase, and mammalian pancreatic lipases and peptidases, Preferred esterases include chymotrypsin (E.C. 3.4.21.1) because of its high stereoselectivity, and broad substrate range. Other esterases include, but are not limited to, carboxyl esterase (E.C. 3.1.1.1.), carboxypeptidase A (E.C. 3.4.17.1), acetyl cholinesterase (E.C. 3.1.1.7), pepsin (E.C. 3.4.23.1), trypsin (E.C. 3.4.21.4) and papain (E.C. 3.4.22.2).

Amino acid residue sequences for natural enzymes, and published modified enzymes, useful for the present invention are generally available in the published literature and on computer data bases. Preferred and widely used protein sequence data bases include Geneseq™, GenBank®, EMBL, Swiss-Prot, PIR and GenPept, all of which are commercially available from Intelligenetics, Inc. (Mountain View, Calif.).

The complete three-dimensional structure for many enzymes suitable for use in this invention are available from the Brookhaven Protein Data Bank, Brookhaven National Laboratories, Upton, N.Y. Exemplary proteins with their respective Protein Data Bank Codes (PDB numbers) that are included in the data base include:

(1hvp): hiv-1 protease complex with substrate;
(2hvp): hiv-1 protease; (3hvp): (aba==67,95==)-hiv-1 protease,sf2 isolate; (4hvp): hiv-1 protease complex with the inhibitor n-acetyl-*thr-*ile-*nle-psi(ch2-nh)-*nle-*gln-*arg amide (mvt-101) (SEQ ID NO 1); (2cyp): cytochrome c peroxidase (e.c.1.11.1.5);
(1gp1): glutathione peroxidase (e.c.1.11.1.9);
(4cat): catalase (e.c.1.11.1.6);
(7cat): catalase (e.c.1.11.1.6); (8cat): catalase (e.c.1.11.1.6); and (2sod): cu,zn superoxide dismutase (e.c.1.15.1.1).

Particularly preferred are the antioxidant enzymes of the superoxide dismutase (SOD) class. Because of the wide distribution of SOD enzymes in aerobic organisms, many isolates of SOD have been reported in many species. A recent literature search revealed descriptions of the sequence of 26 different SOD enzymes in mammals, non-mammals, bacteria, yeast and plants including human EC-SOD, [Hjalmarsson et al., *Proc. Natl. Acad. Sci. USA*, 84:6340–6344 (1987)]; human SOD [Sherman et al., *Natl. Acad. Sci. USA*, 80:5465–5469], and Schneider et al., *Cell*, 54:363–368 (1988); bovine SOD [Steinman et al., *J. Biol. Chem.*, 249:7326–7338, (1974)]; equine SOD [Lerch et al., *J. Biol. Chem.*, 256:11545–11551 (1981)];. murine SOD [Getzoff et al., *Proteins: Struct. Func. Genet.*, 5:322–336 (1989)]; porcine SOD [Schinina et al., *FEBS Lett.*, 186:267–270 (1985)]; rabbit SOD [Reinecke et al., *Biol. Chem., 369:715–725* (1988)]; ovine SOD [Schinina et al., *FEBS Lett.*, 207:7–10 (1986)]; rat SOD [Steffens et al., *Z. Physiol. Chem.*, 367:1017–1024 (1986)]; drosophila SOD [*Nucleic Acids Res.*, 17:2133–2133 (1989)]; xenopus SOD [*Eur. J. Biochem.* (1989)]; brucella SOD [Beck et al., *Biochemistry*, 29:372–376 (1990)]; caulobacter SOD [Steinman et al., *J. Bacteriol.* (1988)]; neurospora SOD [Lerch, *J. Biol. Chem.*, 260:9559–9566 (1985)]; photobacterium SOD [Steffens et al., *Z. Physiol. Chem.*, 364:675–690 (1983)]; schistosoma SOD [Simorda et al., *Exp. Parasitol.*, 67:73–84 (1988)]; yeast SOD [Steinman et al., *J. Biol. Chem.*, 255:6758–6765 (1980)]; cauliflower SOD [Steffens et al., *Biol. Chem. Hoppe-Seyler*, 367:1007–1016 (1986)]; cabbage SOD [Steffens et al., *Physiol. Chem.*, 367:1007–1016 (1986)]; maize SOD [Cannon et al., *Proc. Natl. Acad. Sci. USA*, 84:179–183 (1987)]; pea SOD [Scioli et al., *Proc. Natl. Acad. Sci. USA*, 85:7661–7665 (1988)]; spinach SOD [Kitagawa et al., *J. Biochem.*, 99:1289–1298 (1986)]; and tomato SOD [*Plant Mol. Biol.*, 11:609–623 (1988)]. Any of these varieties of SOD are suitable for use as a D-enzyme of the present invention.

Carbonic anhydrase C is another preferred enzyme suitable for the preparation of a D-enzyme. Carbonic anhydrase C catalyses the reaction that combines carbon dioxide and water to form bicarbonate and hydrogen ions. The sequence of carbonic anhydrase C is described by Henderson et al., *Biochim. Biophys. Res. Comm.*, 52:1388 (1973); Lin et al., *J. Biol. Chem.*, 249:2329 (1974).

Other optically specific enzymes that react with a chiral substrate and are therefore useful as a D-enzyme of this invention have been extensively described in U.S. Pat. Nos. 5,077,217, 5,057,427, 4,800,162, and 4,795,704, which are specifically incorporated herein by reference.

C. Synthesis of a D-Enzyme

A D-enzyme of the present invention can be prepared by any means available to one skilled in the polypeptide arts. The precise method employed for synthesizing the polypeptide is not considered essential to the basic structure of a D-enzyme of this invention, and therefore is not to be considered as limiting, particularly as technology develops new ways to synthesize and assemble polypeptides.

Preferred routes of polypeptide synthesis include:
1. Conventional chemical synthesis, e.g. step wise synthesis, and
2. Assembly of polypeptide building blocks by chemical ligation.

It is presently considered impractical to employ conventional chemical (step-wise) synthetic methods to produce polypeptides having more than 100 amino acid residues. On the other hand, chemical ligation methods may be employed to assemble polypeptides several time larger. Accordingly, for D-enzymes greater than 100 amino acid residues, chemical or enzymatic ligation techniques are presently the only practical means for making such products. Described herein is a ligation strategy for preparing 10–100 milligram amounts of the D- and L-HIV-1 protease enzymes.

Although not presently available, manufactured protein synthesis apparati using D-proteins may solve the problem of incorporating D-amino acids in the protein translation machinery, making it possible to synthesis D-enzymes using recombinant DNA expression of messenger RNA and D-amino acids.

Conventional Step-wise Syntheses

Synthetic chemistry techniques, such as the stepwise addition of amino acids in a solid-phase Merrifield-type synthesis, are preferred for reasons of purity, antigenic specificity, freedom from undesired side products, ease of production and the like. An excellent summary of the many techniques available for synthesizing L-proteins and enzymes can be found in Steward et al., in "Solid Phase Peptide Synthesis", W.H. Freeman Co., San Francisco, 1969; Bodanszky et al., in "Peptide Synthesis", John Wiley & Sons, Second Edition, 1976 and Meienhofer, in "Hormonal Proteins and Peptides", Vol. 2, p. 46, Academic Press (New York), 1983; and Kent, Ann. Rev. Biochem., 57:957, 1988, for solid phase peptide synthesis, and Schroder et al., in "The Peptides", Vol. 1, Academic Press (New York), 1965 for classical solution synthesis, each of which is incorporated herein by reference. Appropriate protective groups usable in such synthesis are described in the above texts and by McOmie, in "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

For the synthesis of a D-enzyme, D-amino acids or protected D-amino acids are utilized rather than the conventional L-amino acids. D-amino acids suitable for polypeptide synthesis are commercially available from the Peptide Institute (Osaka, Japan); Peptides International (Louisville, Ky.); Bachem Bioscience (Philadelphia, Pa.); and Bachem California, (Torrance, Calif.).

Using a solid phase synthesis as exemplary, the protected or derivatized D-amino acid is attached to an inert solid support through its unprotected carboxyl or amino group. The protecting group of the amino or carboxyl group is then selectively removed and the next D-amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added D-amino acid residue, and the next D-amino acid (suitably protected) is then added, and so forth. After all the desired D-amino acids have been linked in the proper sequence, any remaining terminal and side group protecting groups (and solid support) are removed sequentially or concurrently, to afford the final polypeptide.

Ligation Techniques

The chemical ligation of polypeptides has recently been described by Kent in U.S. application Ser. No. 07/865,368, filed Apr. 8, 1992, whose disclosures are hereby incorporated by reference. This technique is preferred for D-enzymes having a length of 100 amino acid residues or greater. In this procedure, two polypeptides are first synthesized, and contain termini adapted for chemical ligation. After stepwise chemical synthesis and cleavage from their respective solid phase resins, the two polypeptides are mixed and reacted to join the adapted termini and form a larger, linear polypeptide comprised of the two polypeptides.

An exemplary step-wise synthesis of a D-enzyme is detailed in Example 1 describing the synthesis of a variety of D-HIV-1 protease. Example 5 discloses an exemplary ligation-type synthesis of D- and L-[Aba$^{67,95}$(CO—S)$^{51-52}$]$_2$HIV-1 protease analogs. The D-[Aba$^{67,95}$(CO—S)$^{51-52}$]$_2$HIV-1 protease analog of Example 5 is functionally equivalent to the D-HIV-1 protease of Example 1.

Similar synthesis can be applied to the preparation of D-superoxide dismutase, carbonic anhydrase, or any of the other D-enzymes described herein.

D. Methods for Screen Chemical Libraries

The most common means for identifying pharmaceutically useful compounds involves screening chemical libraries. The thoroughness such screening may be markedly enhanced by employing both L-enzymes and D-enzymes.

Natural product libraries isolated from nature may consist of several hundred thousand compounds. Chemical libraries may also be prepared by chiral synthesis of particular enantiomers or by non-chiral synthesis of racemates. In the search for new drug candidates, such libraries may be screened to identify compounds active in a particular assay. In many instances, the target molecule is an enzyme or an enzyme system and the search is directed to identifying drug candidates which can serve as specific inhibitors or cofactors of such enzyme or enzyme system. Once a candidate compound is identified as an inhibitor of a specific therapeutically relevant enzyme, analogues of such candidate compound may be designed and synthesized so to improve its activity and other desireable properties.

In many instances, chiral specificity is a necessary attribute of active substrates, cofactor, and inhibitors. However, it is disclosed herein that the chiral specificity of substrates, cofactors, and inhibitors depends upon the chirality of the target enzyme. Accordingly, the target enzyme can often distinguish between active and inactive enantiomers of a given a substrate, cofactor, and inhibitor. Component elements of a natural product library often display random chirality and bear to inherent relationship to the target enzyme. Accordingly, if only a single enantiomer is present within a library, the chirality of such enantiomer is as likely to be the wrong (inactive) enantiomer as to be the right (active) with respect to any given target enzyme. If the library is screened against only the native (L)-configuration of a target enzyme, and if the elements of the library are non-racemate, i.e. if they are chiral, there is a significant chance (50/50) that the library include only the inactive enantiomer.

The present invention teaches that screening a natural product library against both an L-enzyme and its corresponding D-enzyme, can approximately double the number of candidate compounds identified from such library.

Any candidate compound identified as active against a D-enzyme may be inactive with respect to the corresponding L-enzyme. However, structural analysis of a candidate compound active with respect to a D-enzyme is predictive of the structure of a candidate compound active with respect to the corresponding L-enzyme, i.e. the enantiomers of compounds found to be active with respect to a D-enzyme are likely to have corresponding activity with respect to the corresponding L-enzyme.

Accordingly, the number of candidate compounds positively identified from a chemical or natural product library may be significantly enhanced if the library is screened against both the L- and D-version of the enzyme. For example, screening a natural product library with respect to the inhibition of the protease activity of both L- and D-HIV protease should significantly increase the number candidate drugs identified as active inhibitors.

The above concepts apply equally to screening natural product libraries with respect to receptor activity, i.e. as agonist or antagonist with respect to protein receptors. Included amongst protein receptors against which natural-product and/or chemical libraries may be usefully screened are the following: GPIIb-IIIa and LFA-1, Ruoslahti et al., *Science*, 238: 491–497 (1987); CSAT, Horwitz et al., *J. Cell Biol.*, 101:2134 (1985); VLA-2, Nieuwenhuis et al. *Nature*, 318:470 (1985); CR3 Complement Receptor, Wright et al., *PNAS*, 84:1965 (1987); CR2 Complement Receptor, Nemerow et al., *J. Virol.*, 55: 3476 (1985); CD4 T Cell Receptor, Guyader et al., *Nature*, 320:662 (1987); FRP Receptor, Yu et al., *Nature*, 330:765 (1987); Apolipoprotein Receptor, Yamada et al., *J. Clin. Invest.*, 80: 507 (1987); Interleukin Receptor, Dower et al., *Immunology Today*, 8:46 (1987); Fc Receptor, Anderson et al., *J. Immunol.*, 138: 2254 (1987); Somatostatin Receptor, Kim et al., *J. Biol. Chem.*, 262: 470 (1987); PDGF Receptor, Keating et al., *J. Biol. Chem.*, 252: 7932 (1987); and Transferrin Receptor, Kohgo et al., *Blood*, 70:1955 (1987).

Other proteins having binding sites which may be screened according to the method of the present invention include insulin receptor binding site on insulin, reovirus receptor binding site on the firal hemaglutinin protein, fibrinogen receptor binding site on figrinogen A alpha, thyroid hormone receptor binding sites α and β, LDL receptor binding site on Apo E, lipid A binding site, lecithin-cholesterol acyltransferase (LCAT) binding site on Apo AI, and Mac-1 integrin receptor binding site on fibrinogen D-30.

E. Methods for Producing Chirally Pure Compounds

In another embodiment, the present invention contemplates methods using a D-enzyme of this invention for the production of chirally pure chemical compounds. A chirally pure compound, as used herein refers to a molecule substantially free from its stereoisomer.

The methods can be practiced in a variety of ways. A single chirally pure chemical can be produced by a reaction by D-enzyme upon a racemic mixture of substrates, leaving in the racemic mixture one of the substrate isomers, and converting the other substrate isomer into a product. In this method, the desired chirally pure compound can be a reaction product, or it can be the substrate isomer left unreacted in the racemic mixture, freed from the contaminating isomer by the action of the D-enzyme.

Thus, in this embodiment, the invention contemplates a method of producing a chirally pure chemical comprising:
 a) reacting in an aqueous admixture a first stereoisomer with a D-enzyme that specifically converts said first stereoisomer into a chiral reaction product; and
 b) isolating the chiral reaction product from the admixture, thereby forming the chirally pure chemical. In an alternative version of this embodiment, the aqueous admixture comprises a racemic mixture having at least a first and a second stereoisomer.

The reaction is initiated by admixing D-enzyme with substrate and subjecting the reaction admixture to suitable reaction conditions for driving the enzyme catalyzed reaction. For a D-enzyme those conditions depend upon the particular reaction chemistry to be catalyzed and upon the conditions under which the enzyme is active. The reaction conditions for a D-enzyme are preferably the same as is optimally used for the corresponding reaction of the isomeric substrate by the corresponding L-enzyme. Preferred reaction conditions are those temperature and aqueous buffer conditions which favor maximum enzyme activity for the desired reaction and minimum undesirable side reactions.

The isolating step can be conducted by any chemical manipulation that provides for the resolution of the chirally pure chemical from the reaction product admixture formed in step (a). Exemplary isolating manipulations are well know to the chemist and include solvent extractions, chromatography, selective crystallization, distillation, and the like.

In a related embodiment, the invention contemplates a method for producing a chirally pure chemical comprising:
 a) reacting in an aqueous admixture a racemic mixture having at least a first and a second stereoisomer with a D-enzyme that specifically converts the first stereoisomer into a reaction product; and
 b) isolating said second stereoisomer from said admixture, thereby forming said chirally pure chemical. The reaction is conducted for a time period and under reaction conditions sufficient to convert substantially all of the first stereoisomer into the chiral reaction product.

In this latter embodiment, depletion of the original racemic mixture of an undesirable stereoisomer resolves the chirally pure chemical, and the remaining unreacted stereoisomer is isolated to form the chirally pure chemical.

Chemical synthesis of a chirally pure chemical using a D-enzyme can be conducted in a homogeneous or heterogeneous aqueous reaction environment, or can be conducted in enzyme reactors, where the D-enzyme is in the solid phase, or in membrane reactors, where a solvent or D-enzyme is segregated away from either the reactants or products. Such solid phase enzyme reactors and membrane enzyme reactors, and their methods of use, have been extensively described in U.S. Pat. Nos. 5,077,217, 5,057,427, 4,800,162, and 4,795,704, which are specifically incorporated herein by reference.

F. Methods of Co-Crystallization Racemic Mixtures

In one embodiment, the invention contemplates the use of a D-enzyme to produce an X-diffraction pattern of a crystal for determining the three dimensional structure of a protein. Methods for preparing crystallized proteins and analyzing the crystal structure by the X-ray crystallographic arts is well known. See for example the teaching of Stout et al., in "X-Ray Structure Determination: A Practical Guide", Macmillan, New York, 1968; and Miller et al, *J. Mol. Biol.*, 204:211–212, 1988, which are hereby incorporated by reference.

In a preferred embodiment, the invention contemplates the co-crystallization of the D- and L-HIV-1 protease enzymes prepared as described in Example 1. The resulting crystal, formed by the vapor diffusion crystal growth method described by Miller et al., supra, is used to solve the three dimensional structure of HIV-1 protease using conventional X-ray diffraction methods to produce a racemic crystal due to the presence of the enantiomeric forms (D- and L-) of HIV-1 protease in the crystal.

Such a crystal structure is further useful, for example, to model inhibitors of HIV-1 protease useful for therapeutic treatment of HIV-1 infection by inhibition of the protease.

Co-crystallization of D- & L-HIV protease preparations can generate centrosymmetric crystals for high-accuracy X-ray diffraction studies. This should provide data that can find a wide usefulness in drug design studies for AIDS therapeutics. For this purpose, it is necessary to produce each enantiomorph of the enzyme in hundred milligram quantities without the complication of autolysis during the extraction, purification and folding of the synthetic products. We have disclosed that an HIV-1 protease analogue, prepared by the directed chemical ligation of unprotected peptide segments and containing a thioester replacement for the natural peptide bond between $Gly^{51}$-$Gly^{52}$, has full activity. This segment condensation strategy also largely avoids the possibility of autodigestion by the enzymes during their preparation.

G. Therapeutic Methods

The invention contemplates therapeutic methods involving administration of therapeutically effective amounts of a D-enzyme to a mammal or human, where an L-enzyme would normally be the active ingredient in the therapeutic composition to be administered. By substituting a D-enzyme for its corresponding L-enzyme, the therapeutic enzyme acquires the benefits of a D-enzyme as described herein, including increased effective half-life due to resistance to proteases, and diminished immune recognition.

Enzymes for use in therapeutic treatment methods as a D-enzyme of this invention can be derived from any number of enzymes of known primary amino acid residue sequence that provide therapeutic applications, and which have achiral substrates. Antioxidant enzymes, in particular, have therapeutic applications that can benefit from being in the form of a D-enzyme to increase effective therapeutic half-life.

Antioxidants function as anti-inflammatory agents. The medically important antioxidant enzymes of known structures are superoxide dismutase, catalase and glutathione peroxidase. These enzymes are involved in the prevention of post-ischemic injuries and the control of inflammatory disorders. Wilsman et al., In: *Superoxide and Superoxide Dismutase in Chemistry, Biology and medicine*, Rotilio, Ed., Elsevier Science, Amsterdam Publishers (1986). As demonstrated in the case of SOD, these enzymes would benefit from an increased circulatory half-life.

1. Superoxide Dismutase

The SOD enzymes, which catalyze the conversion of superoxide radical to molecular oxygen and hydrogen peroxide, are ubiquitous in organisms that utilize oxygen.

The dismutation reaction of SOD enzymes is important in preventing tissue damage by free radicals. Indeed, the effectiveness of human intracellular SOD (HSOD) in relieving inflammatory disorders including osteoarthritis has been demonstrated by clinical studies in humans. See, Wilsmann, *Superoxide and Superoxide Dismutase in Chemistry, Biology and Medicine*, Elsevier, 500-5 (1986). Additionally, animal studies have suggested that SOD enzymes have therapeutic potential for viral infections. See, Oda et al., *Science*, 244:974–6 (1989). SOD enzymes have also been implicated in preventing alloxan diabetes [Grankvist et al., *Nature*, 294:158 (1981)] and in preventing metastasis of certain forms of cancer (EPO Application No. 0332464).

Therefore in one embodiment, methods for reducing tissue damage caused by oxygen free radical (superoxide) in vivo or in vitro are contemplated by the present invention, using a D-superoxide dismutase (D-SOD) enzyme of this invention.

Human recombinant SOD can protect ischemic tissue in experimental models when injected into the circulation just prior to reperfusion (Ambrosio et al. Circulation 75:282. 1987). Injury to the endothelium, a tissue covered with glycosaminoglycans, is a major consequence of ischemia/reperfusion injury. This causes edema formation due to the loss of barrier function and favors platelet adhesion to endothelium. The protective action of SOD is due to its scavenging of superoxide anion. SOD can also protect the endothelium "in vivo" by preventing the formation of peroxynitrite, which is toxic due to its decomposition to form potent, cytotoxic oxidants (Beckman et al. Proc. Natl. Acad. Sci. USA 87:1620–1624. 1990). Postischemic injury involving the superoxide anion has been observed in the heart, intestine, liver, pancreas, skin, skeletal muscle, kidney and perhaps occurs in other organs (McCord Fed. Proc. 46:2402–2406. 1987). SOD chemically linked or conjugated to albumin exhibits an increased "in vivo" half-life, i.e. slower clearance. Such conjugated SOD has been shown to be superior to unconjugated SOD with respect to inhibiting postischemic reperfusion arrhythmias (Watanabe et al. Biochem. Pharmacol. 38:3477–3483. 1989). The preparation of D-SOD having a half-life greater than the half-life of L-SOD facilitates the use of SOD for preventing or diminishing postischemic damage. SOD has also proven to be effective in several inflammatory diseases like osteoarthritis and rheumatoid arthritis. Local infiltration of SOD in extra-articular inflammatory processes (e.g., tendinitis, tendovaginitis, bursitis, epicondylitis, periarthritis) has also proven to be effective. Improvement upon SOD administration has also been observed in Peyronie's disease and Dupuytren's contracture (Wilsman. In Rotilio Ed. Superoxide and Superoxide Dismutase in Chemistry, Biology and Medicine. Elsevier. 1986). For these inflammatory disorders as well as for respiratory distress syndromes a cell surface targeted SOD with increased half-life will be a useful drug. Organ transport and organ transplant also can benefit from such an improved SOD. In addition, tissue targeted SOD should help alleviate the toxic secondary effect of anti-cancer radio- and chemotherapy. Drug (antibiotic and anticancer) induced nephritis also can be reduced by a more potent SOD. D-SOD may be substituted to advantage for L-SOD in the aboverecited therapeutic applications.

Thus, the present invention contemplates a method of in vivo scavenging superoxide radicals in a mammal that comprises administering a therapeutically effective amount of a physiologically tolerable composition containing a D-SOD enzyme to a mammal in a predetermined amount calculated to achieve the desired effect.

For instance, when used as an agent for scavenging superoxide radicals, such as in a human patient displaying the symptoms of inflammation induced tissue damage such as during an autoimmune disease, osteoarthritis and the like, or during a reperfusion procedure to reintroduce blood or plasma into ischemic tissue such as during or after surgical procedures, trauma, in thrombi, or in transplant organs, or after episodes of infection causing massive cell death and release of oxidants, the D-SOD enzyme is administered in an amount sufficient to deliver 1 to 50 milligrams (mg), preferably about 5 to 20 mg, per human adult, when the D-SOD enzyme has a specific activity of about 3000 U per mg. A preferred dosage can alternatively be stated as an amount sufficient to achieve a plasma concentration of from about 0.1 ug/ml to about 100 ug/ml, preferably from about 1.0 ug/ml to about 50 ug/ml, more preferably at least about 2 ug/ml and usually 5 to 10 ug/ml.

D-SOD enzymes having superoxide dismutase (SOD) activity for use in a therapeutic composition typically have about 200 to 5000 units (U) of enzyme activity per mg of protein. Enzyme assays for SOD activity are well known, and a preferred assay to standardize the SOD activity in a D-enzyme is that described by McCord et al., *J.Biol.Chem.*, 244:6049 (1969).

For treating arthritic conditions such as rheumatoid arthritis, tendinitis, bursitis or the like, a dosage of about 1 to 20 mg, preferably about 4 to 8 mg is administered intra articularly per week per human adult. In certain cases, as much as 20 mg can be administered per kilogram (kg) of patient body weight.

For treating reperfusions, or myocardial injuries, a dosage of 5 mg per kg of body weight is preferred to be administered intravenously.

The therapeutic compositions containing a D-SOD enzyme are conventionally administered intravenously, or intra articularly (ia) in the case of arthritis, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Additional exemplary therapeutic applications of SOD, which are directly applicable to the present methods of using therapeutic D-SOD, and compositions containing SOD useful therefor, are described in U.S. Pat. Nos. 5,084,390, 5,006,333 and 4,656,034, which disclosures are specifically incorporated herein by reference.

Similarly to the improved therapeutic methods described above with D-SOD, many otherwise satisfactory enzyme pharmaceutical agents are expected to find limited therapeutic use due to their short lifetimes in vivo. Thus, a convenient method for extending the useful lifetimes of proposed pharmaceutical agents is desired and is provided by the preparation of a D-enzyme according to the present invention. The methods herein allow the preparation of the D-enzyme variants of the enzyme pharmaceutical agents that at least have biological activities comparable to those for the unaltered agent.

H. Therapeutic Compositions

Many of the compounds and groups involved in the instant specification (e.g., D-amino acid residues) have a number of forms, particularly variably protonated forms, in equilibrium with each other. As the skilled practitioner will understand, representation herein of one form of a compound or group is intended to include all forms thereof that are in equilibrium with each other.

In the present specification, "uM" means micromolar, "ul" means microliter, and "ug" means microgram.

Therapeutic compositions of the present invention contain a physiologically tolerable carrier together with a D-enzyme, as described herein, dissolved or dispersed therein as an active ingredient.

As used herein, the terms "pharmaceutically acceptable", "physiologically tolerable" and grammatical variations thereof, as they refer to compositions, carriers, diluents and reaaents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an amount of a D-enzyme of the present invention sufficient to deliver a catalytic amount of the enzyme to the target tissue to be treated. Typically this is an amount of at least 0.1 weight percent, and more preferably is at least 1 weight percent, of D-enzyme per weight of total therapeutic composition. A weight percent is a ratio by weight of protein to total composition. Thus, for example, 0.1 weight percent is 0.1 grams of D-enzyme per 100 grams of total composition.

EXAMPLES

The following examples are intended to illustrate, but not limit, the scope of the invention.

1. Conventional Step-wise Synthesis of L- and D-[Aba$^{67,95,167,195}$]HIV-1 Protease (HIV-1 PR)

Advances in the total chemical synthesis of proteins made possible the reproducible production of homogeneous crystalline L-[Aba$^{67,95,167,195}$]HIV-1 protease (HIV-1 PR). See, for example Kent, *Annu. Rev. Biochem.*, 57:957, (1988); Wlodawer et al., *Science*, 245:616 (1989); and Miller et al., *Science*, 246;1149 (1989).

HIV-1 protease (HIV-1 PR) is a virally-encoded enzyme which cuts polypeptide chains with high specificity and which is essential for the replication of active virions. Kohl et al., *Proc. Natl. Acad. Sci. U.S.A.*, 85:4686, 1988. The 21,500 dalton HIV-PR molecule is made up of two identical 99 amino acid polypeptide chains.

The total chemical synthesis of D-[Aba$^{67,95,167,195}$]HIV-1 protease was carried out as described below, and the properties (covalent structure, physical properties, circular dichroism, enzymatic activity) of the D- and L-enantiomeric forms of this HIV-1 protease enzyme were compared.

To that end, in separate chemical syntheses, the protected polypeptide chains corresponding to the L- and the D-sequences of the [Aba$^{67,95}$] HIV-1 protease 99-aa monomer were prepared by total chemical synthesis. Aba is L- or D-a-amino-n-butyric acid and is used as an isosteric replacement for Cys residues at positions 67 and 95 in the HIV PR monomer polypeptide chain. This same isosteric replacement was used in the work of Wlodawer et al., supra, and Miller et al., supra, leading to the original correct structures of HIV PR.

The chemical synthesis was conducted in conventional stepwise fashion. The 99-aa polypeptide chains were assembled from protected L-amino acids and protected D-amino acids, respectively. The t-Boc D- and L-amino acid derivatives were obtained from the Peptide Institute (Osaka, Japan) and Peptides International (Louisville, Ky.) except: Boc-L-Aba, Boc-L-Asn(Xan), Boc-D-Ile and Boc-D-His (Bom), obtained from Bachem Bioscience (Philadelphia, Pa.); Boc-D-Asn(Xan), Boc-D-Asp(OcHex) and Boc-D-Glu (OcHex), obtained from Bachem California, (Torrance, Calif.); Boc-D-Lys(ClZ), crystallized from the TBA salt obtained from the Peptide Institute; and, D-Aba (Sigma, St. Louis, Mo.) which was converted to Boc-D-Aba and isolated as the DCHA salt. Other side chain protecting groups that were used were: Arg(Tos), Tyr(BrZ), L-His(Tos), D-His (Bom) and Thr(BzL). The L-enantiomer content of the Boc-D-amino acid preparations was between 0.01 and 0.08% [manufacturers specifications]. Stepwise chain assembly was carried out in machine assisted fashion on an Applied Biosystems 430A synthesizer (0.2 mmole scale with D- or L-Boc-Phe-OCH$_2$-Pam-resin). Each cycle of amino acid addition involved: N$^\alpha$-deprotection, neat (100%) TFA [2×30 sec flow washes, plus 1 minute batchwise treatment]; DMF flow wash [1×22 sec, 1×38 sec]; coupling [1×10 minute] with simultaneous in situ neutralization [Boc-amino acid (2.25 mmol) preactivated by reaction with HBTU (2.22 mmol) and DIEA (6.4 mmol) in DMF for 2 min]. The in situ neutralization method has been shown to result in negligible levels of racemization. Henklein et al., in "Innovation & Perspectives in Solid Phase Synthesis", R. Epton Ed., SPPC Ltd., Birmingham, U.K., 1992. The assembled peptides were deprotected and cleaved from the resin in 9:1 HF/p-cresol (resorcinol and thiocresol were present when His(Bom) was included in the sequence) after removal of the Boc group and the formyl group from Trp (with ethanolamine).

The D- and L-products after deprotection were worked up individually, and synthetic enzymes were then prepared by folding the polypeptide polymers from denaturant as described by Wlodawer et al., supra, and Miller et al., supra. To that end, after deprotection and cleavage, the crude peptide products were precipitated with ether and dissolved with 6M guanidine hydrochloride in a pH 8.0 NaHCO$_3$ buffer prior to semi-preparative C18 RP HPLC enrichment and folding by dialysis in 10% glycerol, 25 mM NaH$_2$PO$_4$ buffer pH 7.0. After concentration under high vacuum to a solution in glycerol, the enzymes were quantitated by amino acid analysis and stored at 4° C.

Total yield for the synthesis of L-[Aba$^{67,95,167,195}$] HIV-1 Protease (HIV-1 PR) was approximately 2 milligrams or 0.09%.

Total yield for the synthesis of D-[Aba$^{67,95,167,195}$] HIV-1 Protease (HIV-1 PR) was indeterminant because it was less than 2 milligrams.

2. Structural Analysis of the above L- and D-[Aba$^{67,95,167,195}$]HIV-1 Protease (HIV-1 PR)

The D-enzyme 99-aa monomer, D-[Aba$^{67,95}$] HIV-1 protease, was analyzed for various structural characteristics, and compared to the structural characteristics of the L-isomer. For example, analytical reversed-phase HPLC gave identical retention times for the two synthetic polypeptide chains.

Purified, folded chemically synthesized [Aba$^{67,95}$]HIV-1 protease monomer samples prepared in Example 1 in pH 6.5 MES buffer/10% glycerol were subjected to desalting by reverse phase HPLC. The collected protein peaks were each separately analyzed by ion spray mass spectrometry as described by Bruins et al., *Anal. Chem.*, 59:2642 (1987). Under the conditions used (50% acetonitrile, 50% water, 0.1% TFA) the enzyme is denatured. In the reconstructed mass spectra shown, the raw m/z data have been subjected to a high pass digital filter, then sorted to yield all parent molecular species between 10 kDa and 11 kDa. This reconstruction procedure mathematically reduces the multiple charge states observed for a given molecular species to a single molecular mass.

By reconstructed ion spray mass spectroscopy, the observed monomer molecular mass of the L-enzyme was 10,748±4 daltons (Da), and the mass of the D-enzyme was 10,751±3 Da. Calculated mass: (monoisotopic) 10,748.0 Da; (average) 10,754.7 Da.

Figure 1B:
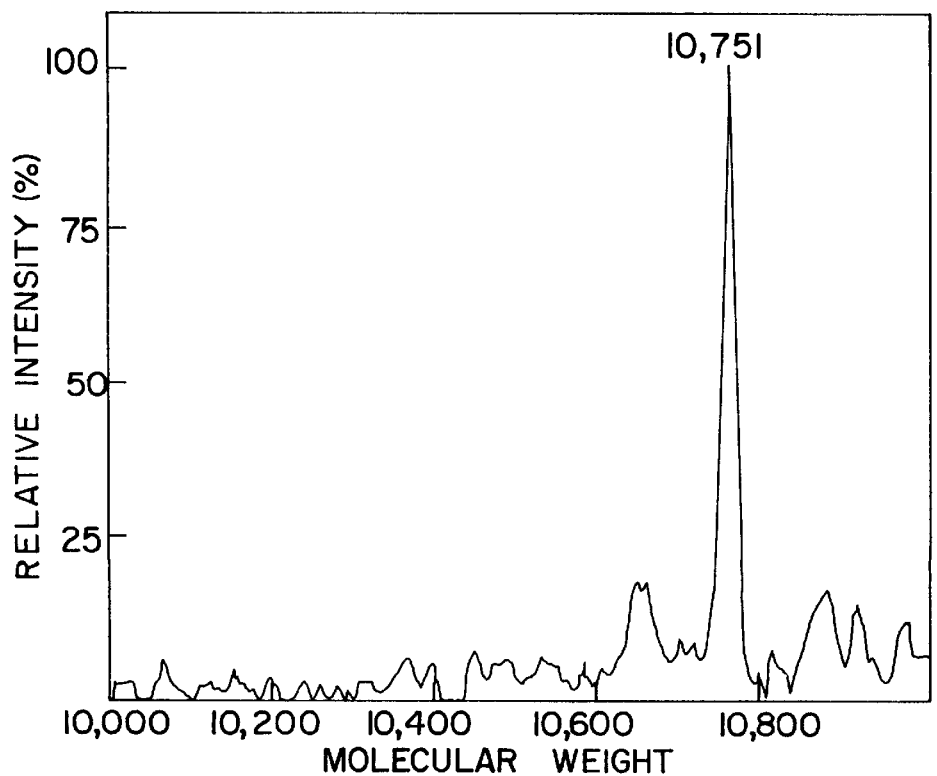
FIG. 1B illustrates data obtained with the D-enzyme.
Figure 2A:
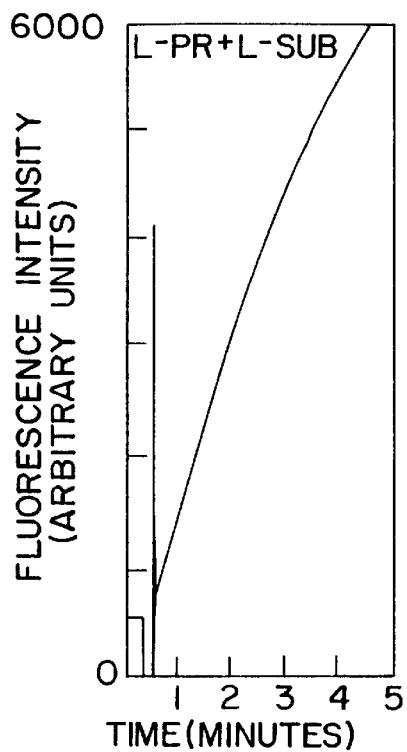
FIG. 2A shows L-enzyme with L-substrate.
Figure 2B:
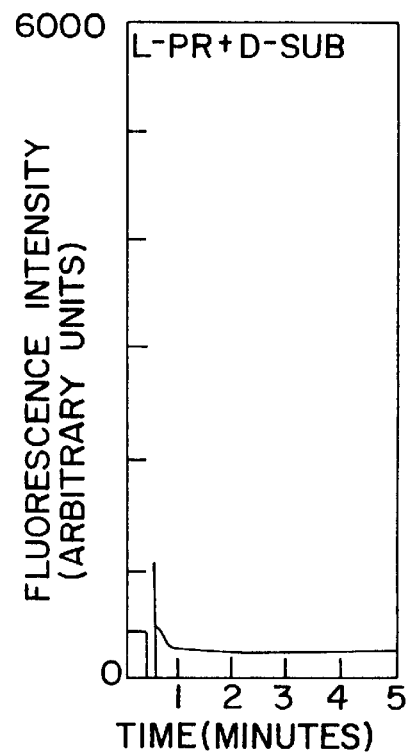
FIG. 2B shows L-enzyme with D-substrate.
Figure 2C:
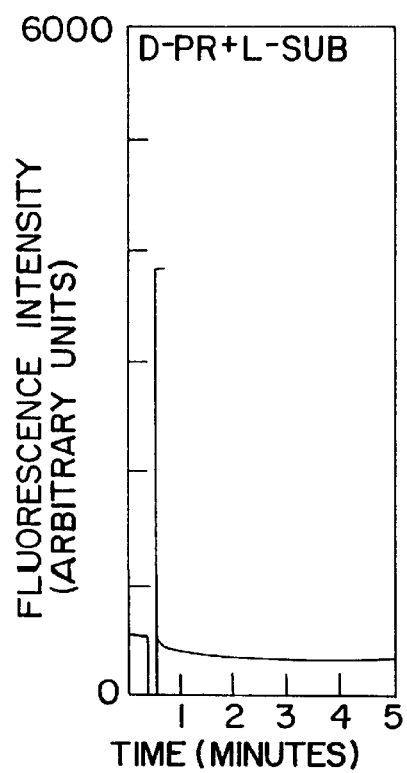
FIG. 2C shows D-enzyme with L-substrate.
Figure 2D:
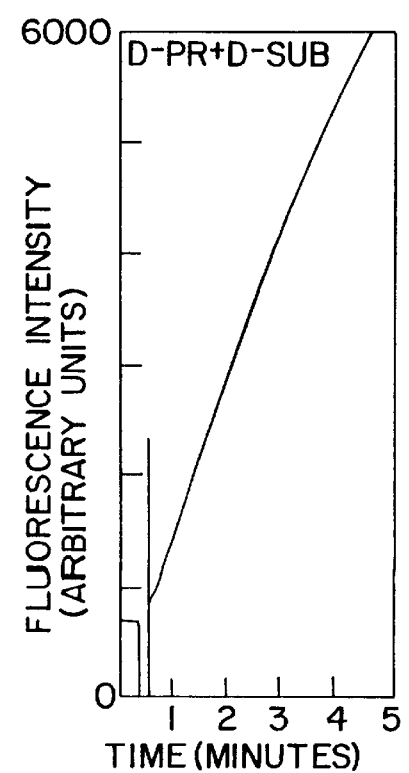
FIG. 2D shows D-enzyme with D-substrate. Data is expressed as activity, measured in arbitrary units of fluorescence intensity, over a reaction time course in minutes.

Thus, the two products (D- and L-enzyme monomers) had the same molecular weight, within experimental uncertainty, when measured by ion spray mass spectrometry. The ion spray mass spectrometry data are shown in FIG. 1.

The complete amino acid sequence of the D-enzyme 99-aa monomer was determined by matrix-assisted laser desorption time-of-flight mass spectrometric readout (Model API-III mass spectrometer, P.E. SCIEX Inc., Thornhill, Toronto, Canada) and was shown to be the same as that of the L-enzyme. Thus, the two synthetic enzyme molecules had identical covalent structure.

On the other hand, differences between the two molecules were revealed in various chiral interactions. Circular dichroism (CD) spectra of the individual D- and L-HIV-1 protease enantiomers were taken over the range 260–195 nm in a pH 5.5 aqueous solution containing 5% glycerol at 25° C. using a 1 mm path length quartz cell on an Aviv CD spectrometer. The CD spectra revealed equal and opposite optical rotations, as expected for enantiomeric protein molecules.

3. Enzymatic Properties of the above L- and D-[Aba$^{67,95,167,195}$]HIV-1 Protease (HIV-1 PR)

The enzymatic properties of the enantiomeric protein comprised of D-amino acids was evaluated and compared to the L-isomer using a fluorogenic assay which employed a hexapeptide analog of a natural GAG cleavage site as substrate as described by Toth et al., Int. J. Peptide Protein Res., 36:544 (1990).

The fluorogenic assays were performed with 15 ul aliquots (corresponding to 1.75 (+10%) ug protein) of each enzyme enantiomer in 10% glycerol, 100 mM MES buffer pH 6.5 added to a solution of 50 mM D- or L-fluorogenic substrate in the MES buffer. The substrate for the enzyme had the sequence 2-aminobenzoyl-Thr-Ile-Nle-Phe(p-NO2)-Gln-Arg.amide. (SEQ ID NO 2). The substrate was synthesized with either D- or L-amino acid derivatives to provide the appropriate enantiomeric forms.

The results of the fluorogenic assay are shown in FIG. 2. Aliquots containing equal amounts (as determined by amino acid analysis) of the purified, folded enzyme preparations were used in the fluorogenic assay. The increase in fluorescence was recorded on a continuous chart recorder. The data illustrate that the two synthetic enzyme molecules were equally active, but revealed a reciprocal chiral specificity in that the L-enzyme cleaved only the L-substrate while the D-enzyme cleaved only the corresponding D-substrate.

In a similar study, the D- and L-enantiomers of the pseudopeptide inhibitor, MVT101 (Ac-Thr-Ile-Nle-psi [CH$_2$NH]-Nle-Gln-Arg.amide), (SEQ ID NO 1) prepared as described by Miller et al., Science, 246:1149 (1989), were evaluated for their effect on the D- and L-HIV protease. The results of the studies using inhibitor are shown in Table 1.

TABLE 1

Chiral inhibitors show reciprocal chiral specificity against D- and L-HIV PR[a].

|          | L-MVT101 | D-MVT101 | Evans Blue[b] |
|----------|----------|----------|---------------|
| L-HIV PR | +        | −        | +             |
| D-HIV PR | −        | +        | +             |

[a]The D- and L-enzymes were separately assayed by the fluorogenic assay method described above using the corresponding chiral substrate, in the presence of 5 × IC50 concentration of inhibitor.
[b]The inhibitor Evans Blue is a non-peptide, achiral mixed competitive-uncompetitive inhibitor of the HIV-1 PR.

The chiral inhibitors were effective only against the corresponding enantiomer of the enzyme, i.e. L-MVT101 inhibited L-HIV PR but not the D-HIV PR-catalyzed reaction, and D-MVT101 inhibited D-HIV PR but had no effect on the L-enzyme-catalyzed reaction. Interestingly, the achiral inhibitor Evans Blue, which shows mixed inhibition kinetics, was a potent inhibitor of both enantiomers of the enzyme (Table 1).

The HIV-1 protease exists as a homodimer; that is, a single enzyme molecule is made up of two identical 99 residue folded polypeptide chains. Wlodawer et al., Science, 245:616 (1989); and Miller et al., Science, 246;1149 (1989). HIV PR is highly active, showing rate enhancement of about 10$^{10}$-fold over uncatalyzed peptide-bond hydrolysis. Kent et al., in "Viral Proteinases as Therapeutic Targets", Wimmer et al., Eds., Cold Spring Harbor Press, Cold Spring Harbor, N.Y., 1989, pp. 223–230; and Richards et al., FEBS Lett., 247:113 (1989). It is a highly specific enzyme which cleaves peptides as well as proteins (Kent et al., supra; and Kroũsslich, et al., Proc. Natl. Acad. Sci. USA, 86:807, 1989) and its specificity is determined by the interactions of the three dimensionally folded enzyme molecule forming a complex with six consecutive amino acid residues in the substrate polypeptide chain. Miller et al., Science, 246;1149 (1989); and Kent et al., supra.

As with all enzymes, HIV PR owes its specificity and catalytic activity to the precise three dimensional structure formed by specific folding of the polypeptide chain, and to precise geometric interactions in the specific complexes formed with substrates. Fersht, in "Enzyme Structure and Mechanism", W. H. Freeman and Company, San Francisco, 1977, pp. 75–81. The observed reciprocal chiral specificities therefore show that the folded forms of the D- and L-enzyme molecules are mirror images of one another in all elements of the three dimensional structure responsible for the enzymatic activity. The extensive nature of these interactions implies that the two enzyme molecules are mirror images in every respect (21), consistent with the observed equal and opposite CD spectra. Most notably, the folded form of the polypeptide backbone (i.e. ignoring the side chains) is itself a chiral entity that must exist in mirror image form in the two protein enantiomers as shown in FIG. 3.

Figure 3A:
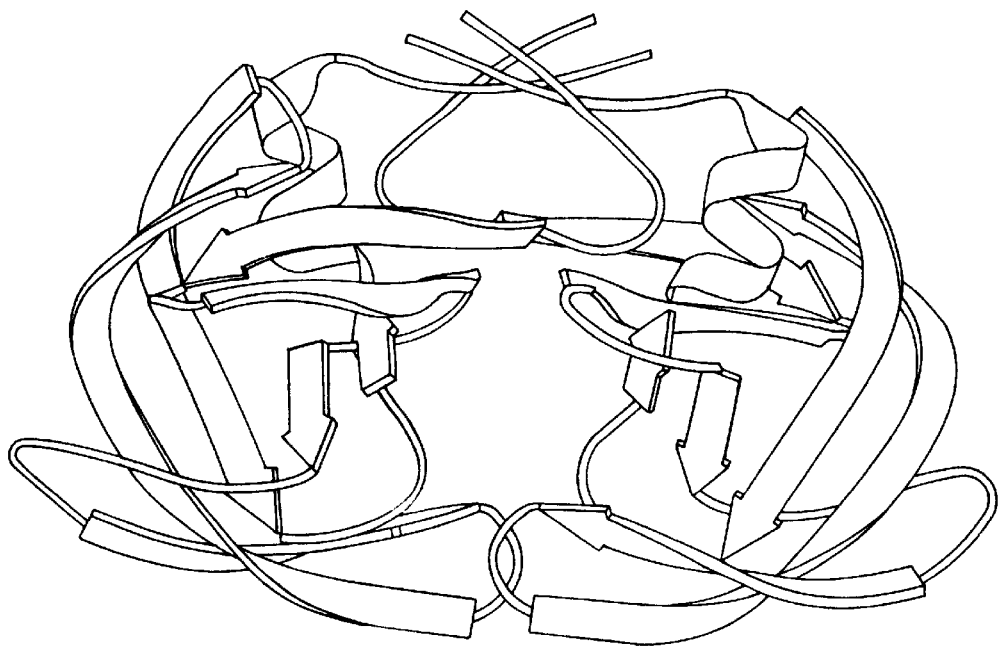
FIGS. 3A and 3B illustrate ribbon representations of the polypeptide backbone of the homodimeric HIV-1 protease molecule in both L- and D-conformations, shown in the left and right portions of the Figure, respectively. The arrows indicate the direction of the polypeptide in the amino- to carboxy-terminus direction.
Figure 3B:
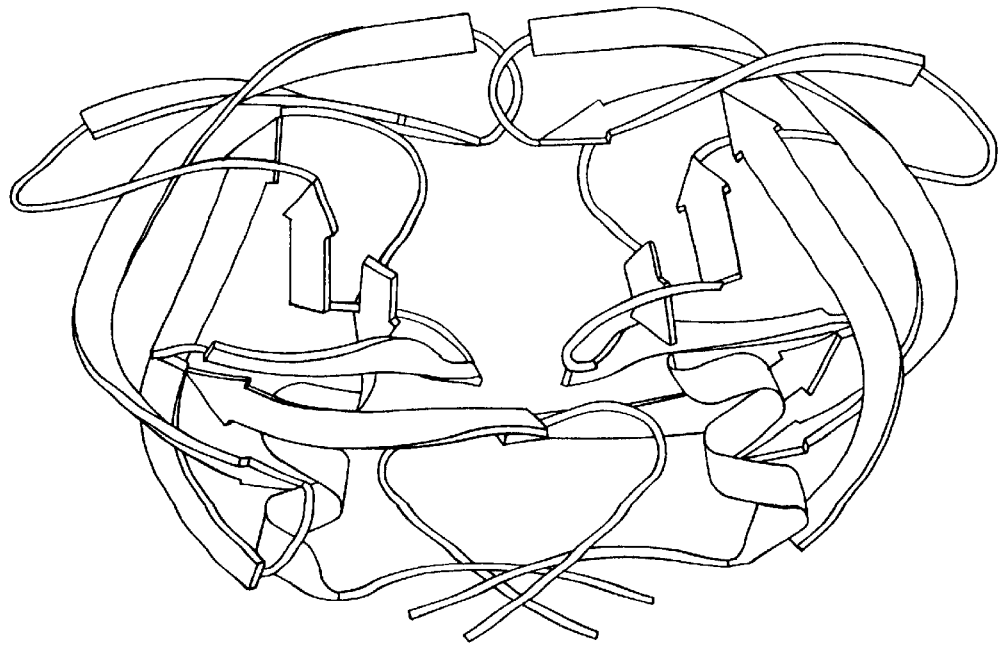

The ribbon representation of L- and D-[Aba$^{67,95,167,195}$] HIV-1 Proteases shown in FIG. 3 is based on the X-ray crystallographic coordinates of the chemically synthesized enzyme when complexed with a substrate-derived peptide inhibitor (inhibitor is not shown) as described by Miller et al., Science, 246:1149 (1989). This model was generated by performing a mirror image transformation of the L-enzyme data.

The folded three-dimensional ribbon "backbone" structures are non-superimposable mirror images and contain numerous chiral elements. These are found in secondary and supersecondary structure, in the tertiary structure and in the quaternary structure as illustrated in FIG. 3. Note, for example, the relatedness of the flaps to one another; the relatedness of the helix segments to the neighboring b-strands; the characteristic twist (right-handed, in the L-protease) of the antiparallel β-strands in each flap described by Richardson et al., in "Protein Folding", Gierasch et al., Eds., American Association of the Advancement of Science, Washington, D.C., 1990, pp. 5–17; and, the handedness of the helical segments. Since the only chiral element introduced in the chemically synthesized polypeptide chains is the stereochemistry at the amino acid Cα atoms (and the Cβ atoms of Thr, Ile), the data presented herein demand that all stereochemical aspects of the folded enzyme molecule, from secondary to quaternary structure, are determined simply by the stereochenistry of the polypeptide backbone. Thus, the present reciprocal chiral properties of the chemically synthesized enzyme enantiomers is a fundamental demonstration that the final folded/three dimensional structure and consequent biological activities of this 21500 dalton homodimeric enzyme molecule are completely determined by the amino acid sequence.

The L- and D-enzymes in this study have never seen biosynthetic conditions, and have thus never been in contact with biochemical factors of any sort. Interestingly, the simple homodimeric enzyme molecule studied here is formed rapidly (both folding and assembly) and accurately even at the relatively low concentrations used in the assay conditions, as well as in more normal dialysis-from-denaturant folding conditions. The results described herein are conclusive evidence that whatever their proposed role, biosynthetic factors are not required for the formation of the correct, functional folded and assembled form of the protein.

The observed reciprocal chiral properties of the mirror-image enzyme molecules described herein reinforces and generalizes the chiral nature of biochemical interactions of proteins. The chiral properties of the protein molecules themselves, which give rise to this behavior, are given only cursory attention in biochemical texts. We can now state, based on experimental evidence, that protein enantiomers will display reciprocal chiral specificity in their biochemical interactions including catalysis.

The observation that both enantiomers of HIV PR were equally affected by the achiral inhibitor Evans Blue provides a number of significant implications. First, the unnatural enantiomer of an enzyme that operates on an achiral substrate and yields an achiral product will be fully functional in vivo. This aspect provides important potential therapeutic applications. Example are carbonic anhydrase and superoxide dismutase. D-Enzymes are expected to be long lived in vivo (in an L-protein biosphere), since they will be resistant to naturally occurring proteases which will in general attack only proteins made up of L-amino acids. D-proteins are comparatively less immunogenic than L-proteins because long polypeptides made up entirely of D-amino acids are not processed and presented as efficiently by the immune system as are polypeptides made up of L-amino acids.

D-Protein molecules have other potential practical applications. For example enzyme enantiomers have utility as chiral catalysts in the selective production of a pure enantiomer of a fine chemical. Enantiomerically pure chemical synthesis has applications to the production of human pharmaceuticals. In addition, protein enantiomers can contribute to the acquisition of phase data in X-ray crystallography as described by Mackay, *Nature*, 342:133 (1989). Centro-symmetric crystals formed by the co-crystallization of a D-, L-protein pair would have greatly simplified phases, and provide more reliable X-ray structural data. At the present time D-enzymes, and D-proteins in general, are accessible only by total chemical synthesis. During ribosomal synthesis of polypeptide chains, even in vitro translation systems, D-amino acids will not be incorporated into growing polypeptides. Ellman et al., *Science*, 255:197 (1992).

4. Discussion of Examples 1–3

D- and L-forms of the enzyme HIV-1 protease are prepared herein by total chemical synthesis. The two proteins have identical covalent structures. However, the folded protein/enzyme enantiomers show reciprocal chiral specificity on peptide substrates. That is, each enzyme enantiomer cuts only the corresponding substrate enantiomer. Reciprocal chiral specificity was also evident in the effect of the enantiomeric inhibitors of the HIV-1 protease enzymes prepared herein. These data show that the folded forms of the chemically synthesized D- and L-enzyme molecules are mirror images of one another in all elements of the three dimensional structure. Enantiomeric proteins display reciprocal chiral specificity in all aspects of their biochemical interactions, retain enzymatic activity, and provide a wide range of useful compositions as described herein.

5. Synthesis and Ligation of D- and L-[Aba$^{67,95}$ (CO—S)$^{51\text{-}52}$]HIV-1 Protease Analogs.

Figure 4:
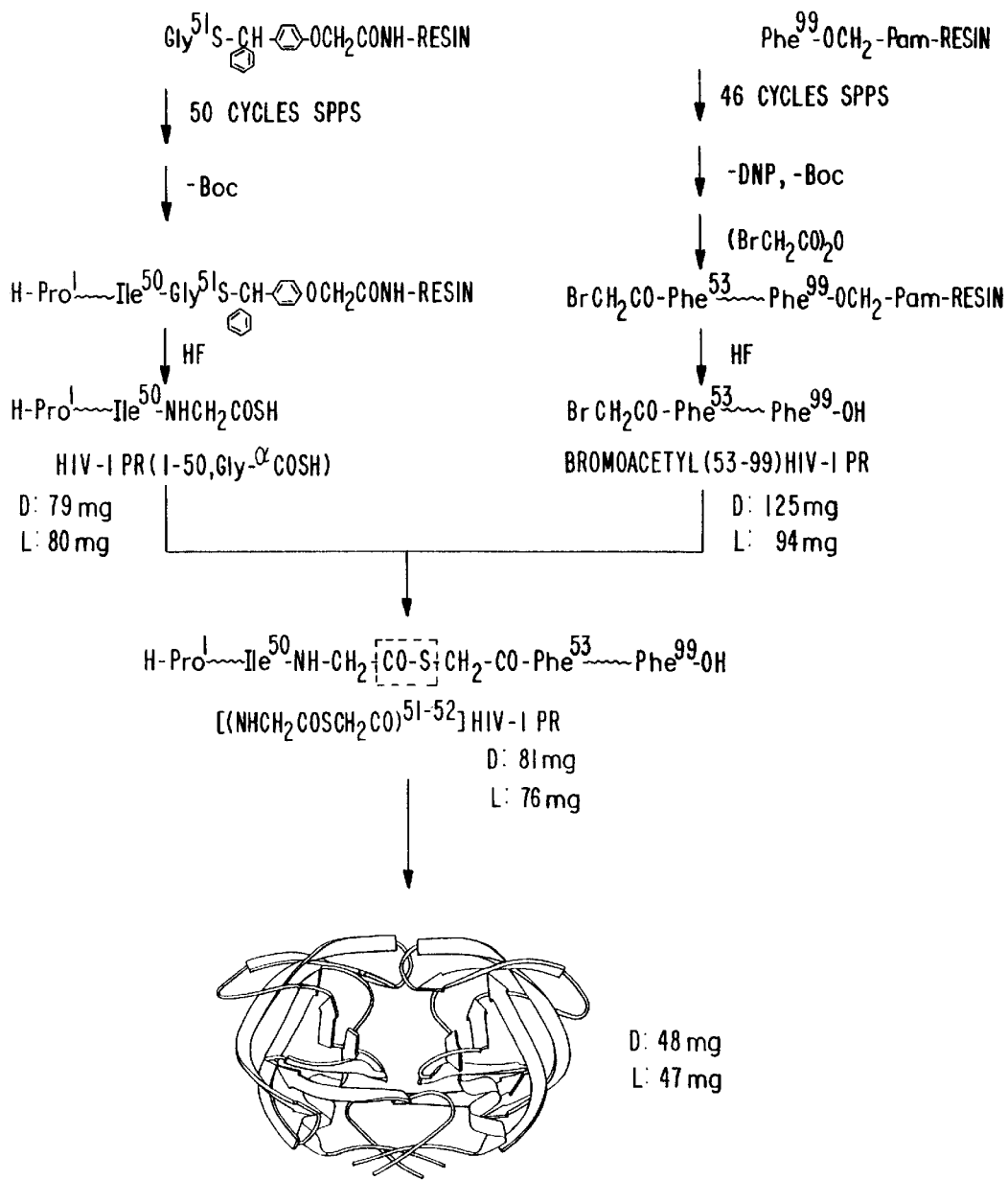
FIG. 4 illustrates a schematic representation of the chemical segment ligation strategy employed for the total synthesis of D- and L-[Aba$^{67,95}$ (CO—S)$^{51-52}$]$_2$ HIV-1 protease analogs.

FIG. 4 illustrates a schematic representation of the strategy employed for the total synthesis of the D- and L-[Aba$^{67,95}$ (CO—S)$^{51\text{-}52}$]$_2$ HIV-1 protease analogues. Protected D- and L-amino acids may be obtained from the Peptide Institute (Osaka, Japan), Peptides International (Louisville, Ky.), Bachem Bioscience (Philadelphia, Pa.) and Bachem California (Torrance, Calif.) and had <0.03% of the opposite enantiomer. HPLC purified, functionalized, unprotected peptide segments, assembled by stepwise solid-phase synthesis, is reacted in the presence of 6M GuHCl to form the ligated 99-residue D- and L-[(NHCH$_2$COSCH$_2$CO)$^{51\text{-}52}$] HIV-1 PR products. (Schnölzer et al., (1992) *Science* 256, 221–225.) The boxed area of FIG. 4 represents the structure of the thioester analogue of the peptide bond Gly$^{51}$-Gly$^{52}$ at the site where the ligation occurred. The thioester serves as a link between the two D-peptides, i.e. the site of ligation. A selenol ester linkage may also be employed for ligating two D-peptides.

Two large peptide segments, i.e. [αCOSH]HIV-1 PR(1–51) and [N$^α$—BrCH$_2$CO]HIV-1 PR(53–99), are assembled, as illustrated in FIG. 5, in separate syntheses by a highly optimized machine-assisted SPPS protocol using Boc-chemistry performed on a modified ABI 430A synthesizer. (Kent et al., "Innovation & Perspectives in Solid-Phase Synthesis", (1992) Ed.

Epton, R. SPPC Ltd. Birmingham, U.K.). The protocol comprised removal of the Na-Boc group with undiluted TFA (2 minute total) followed by a DMF flow wash to give the TFA-peptide-resin salt, and a single 10 minute coupling step using HBTU activated Boc-amino acids and in situ neutralization with DIEA in DMF. Deprotection and coupling reactions are separated by a flow wash step. After purification, the monomers are separately folded by dialysis in the presence of D- & L-MVT-101 inhibitor, respectively, to yield the homodimeric enzymes. The milligram yields of each product are provided in FIG. 4.

The [αCOSH]HIV-1 PR(1–51) peptide may be assembled on 4-[a(Boc-Gly-S)benzylI]phenoxyacetamidomethyl-resin. The [N$^α$—BrCH$_2$CO]HIV-1 PR[53–99] peptide may be prepared by bromo-acetylation of [Aba$^{67,95}$]HIV-1 PR(53–99)-OCH$_2$ Pam peptide-resin. (Yamashiro et al., (1988) *Int. J. Peptide Protein Res.* 31, 322–334.) All peptides are cleaved and deprotected by high HF treatment.

Figure 6:
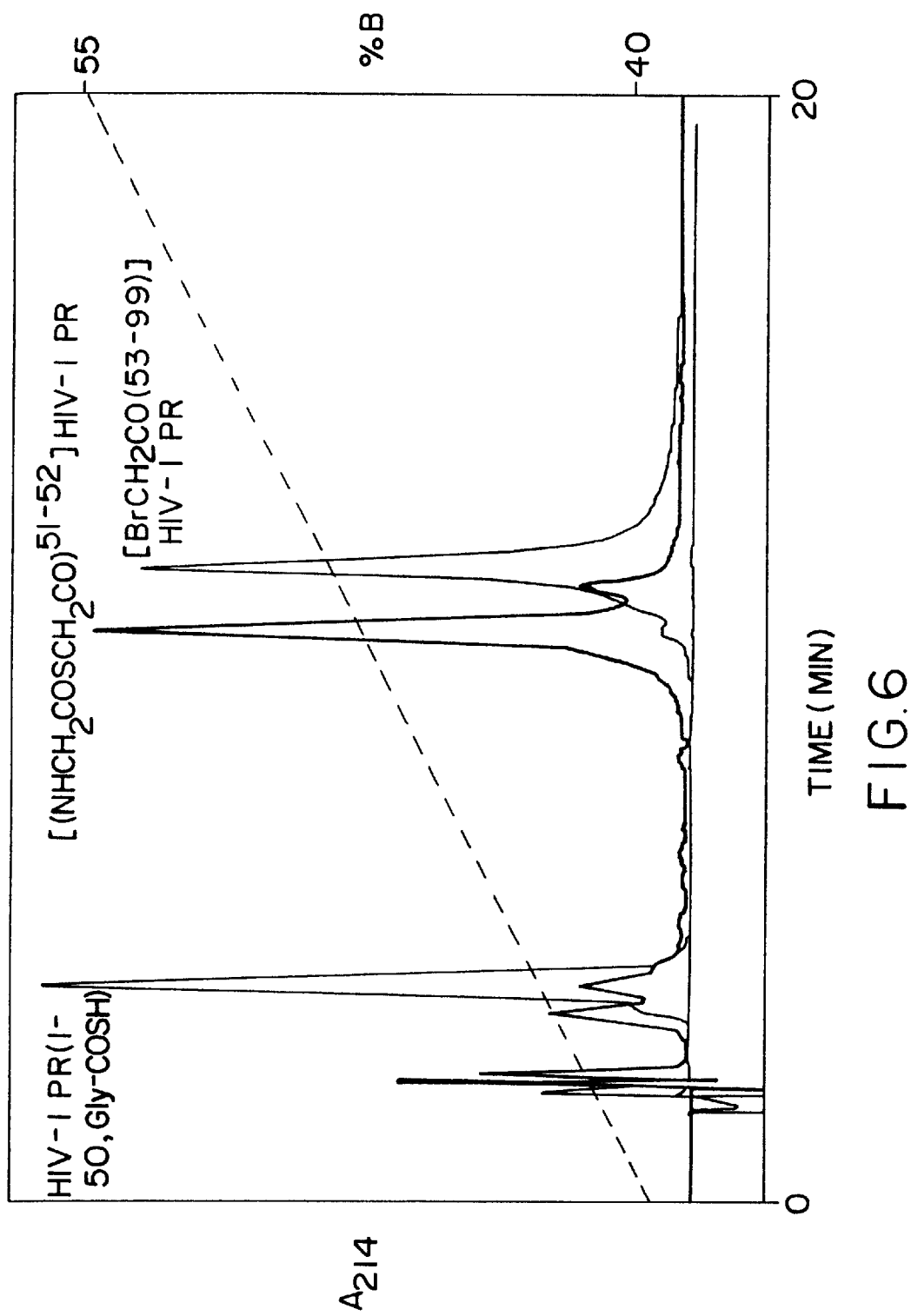
FIG. 6 illustrates a composite chromatogram showing two purified functionalized unprotected D-[αCOSH]HIV-1 PR(1–51) and D-[N$^α$-BrCH$_2$CO]HIV-1 (53–99) segments and the final (48 hour) D-[Aba$^{67,95}$(CO—S)$^{51-52}$]$_2$HIV-1 PR ligation product (bold) fun on a Vydac 218TP5415 column eluted by gradient (40–55% B), at a flow rate of 1 milliliter per minute.
Figure 8A:
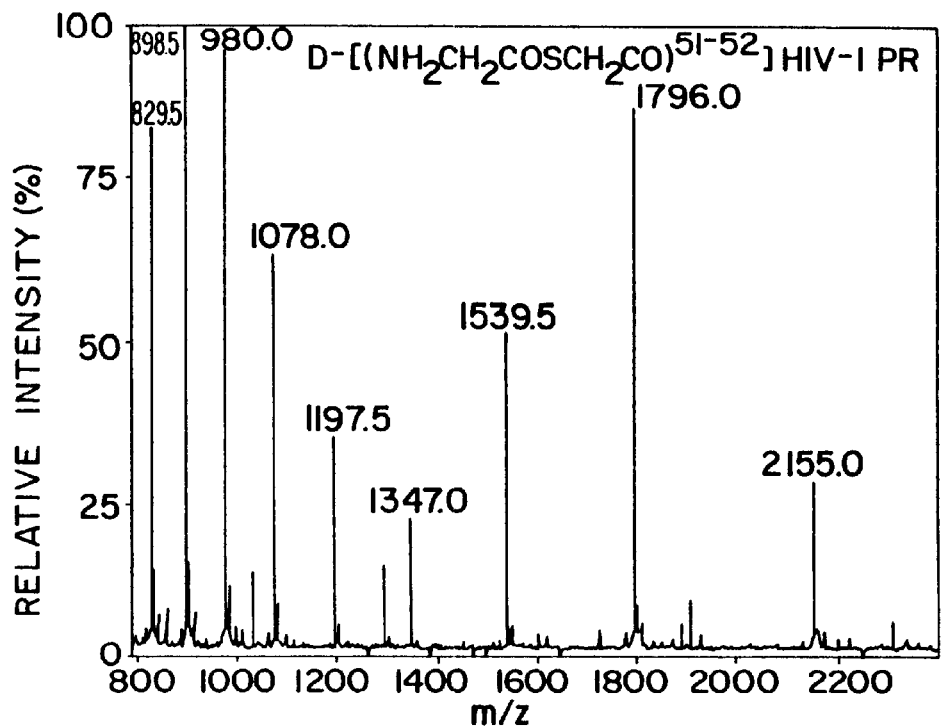
FIGS. 8A–8D illustrate the ion spray mass spectra of the HPLC purified [(NHCH$_2$COSCH$_2$CO)$^{51-52}$HIV-1 PR monomers.
Figure 8B:
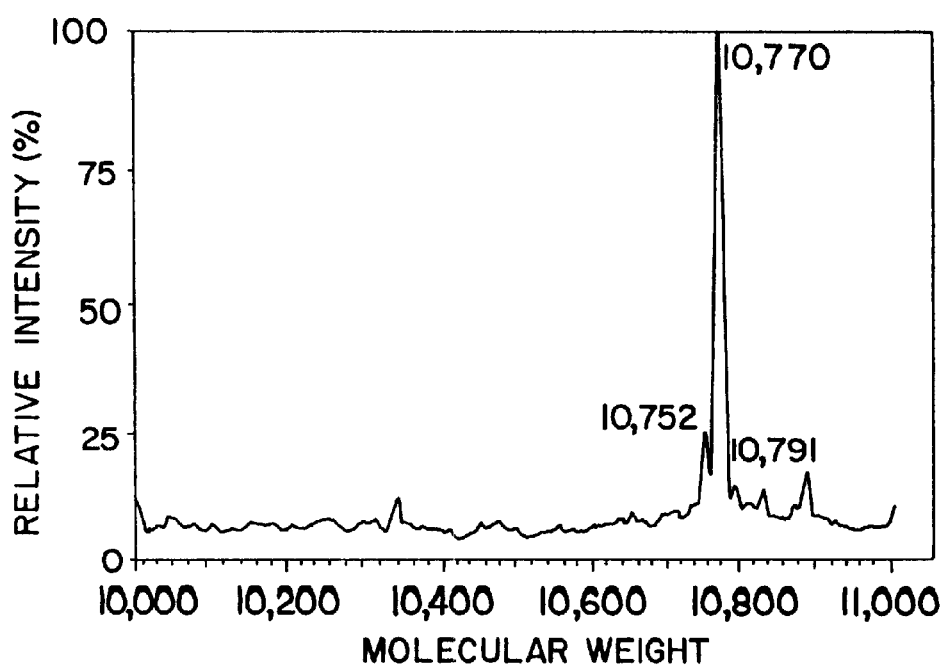
Figure 8C:
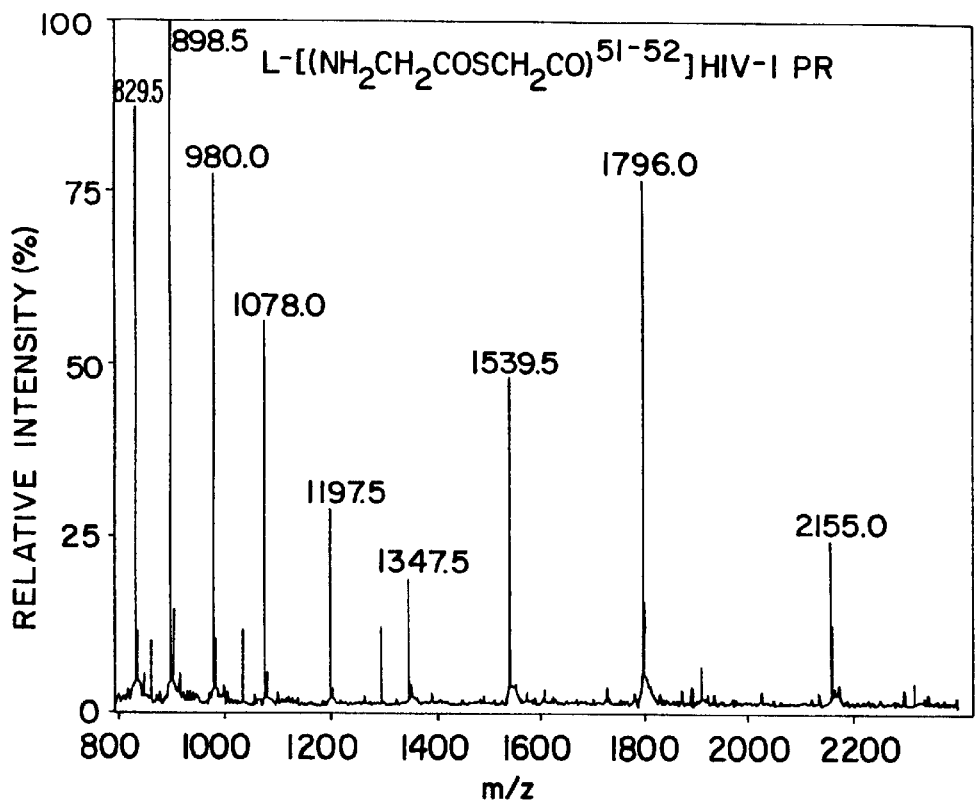
Figure 8D:
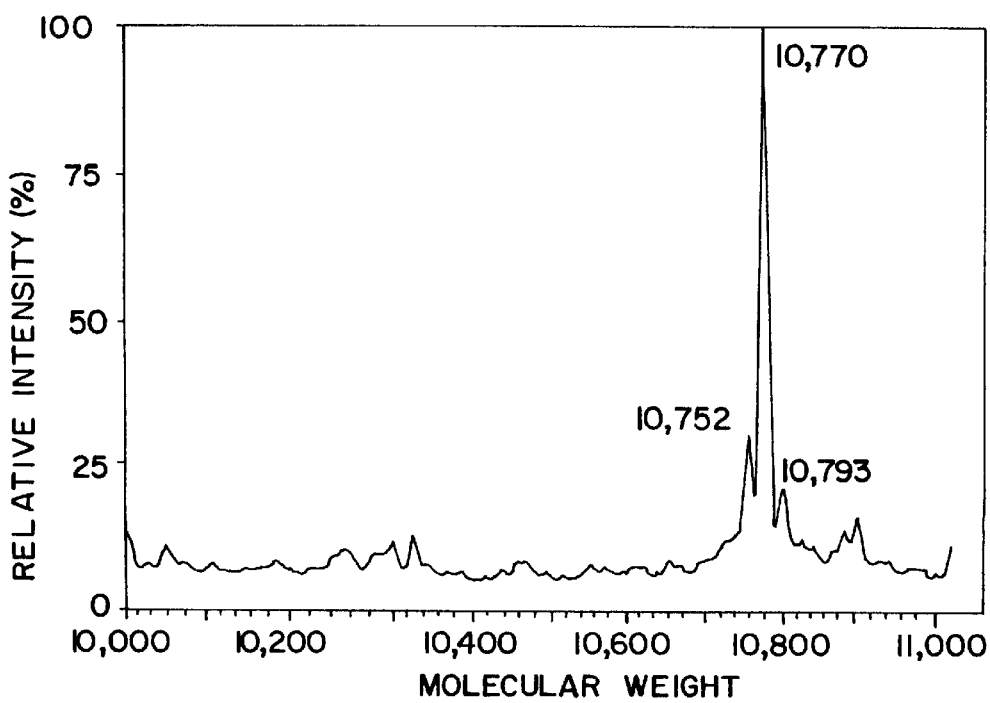
Figure 9A:
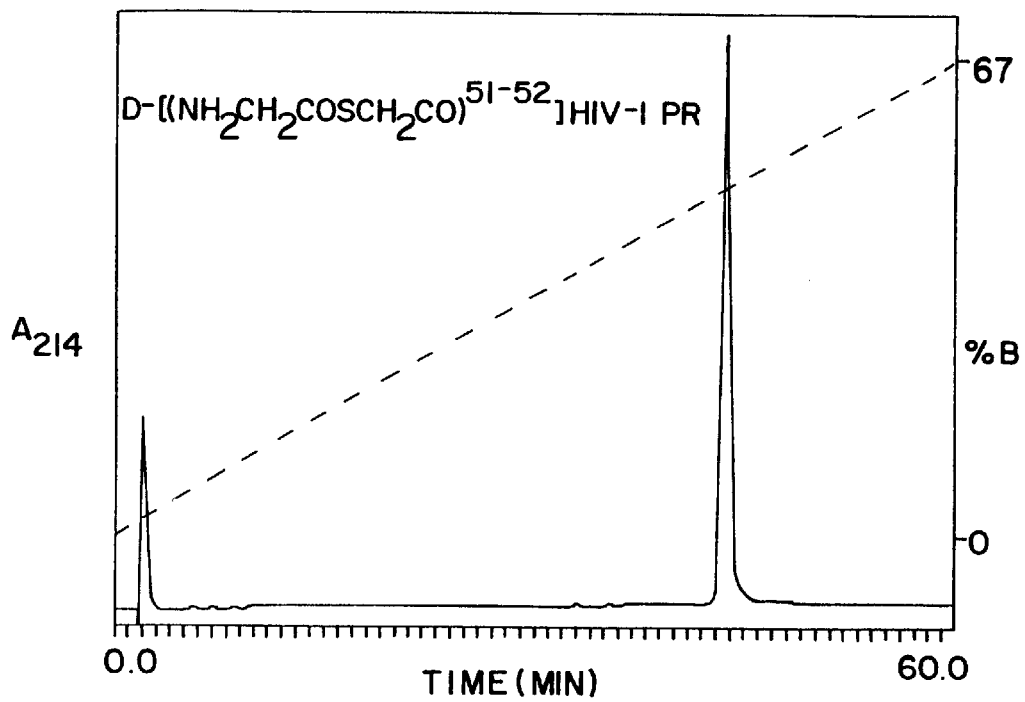
FIGS. 9A–9D illustrate the reverse phase HPLC measurements of D- & L-[Aba$^{67,95}$, (CO—S)$^{51-52}$] HIV-1 PR ligation products.
Figure 9B:
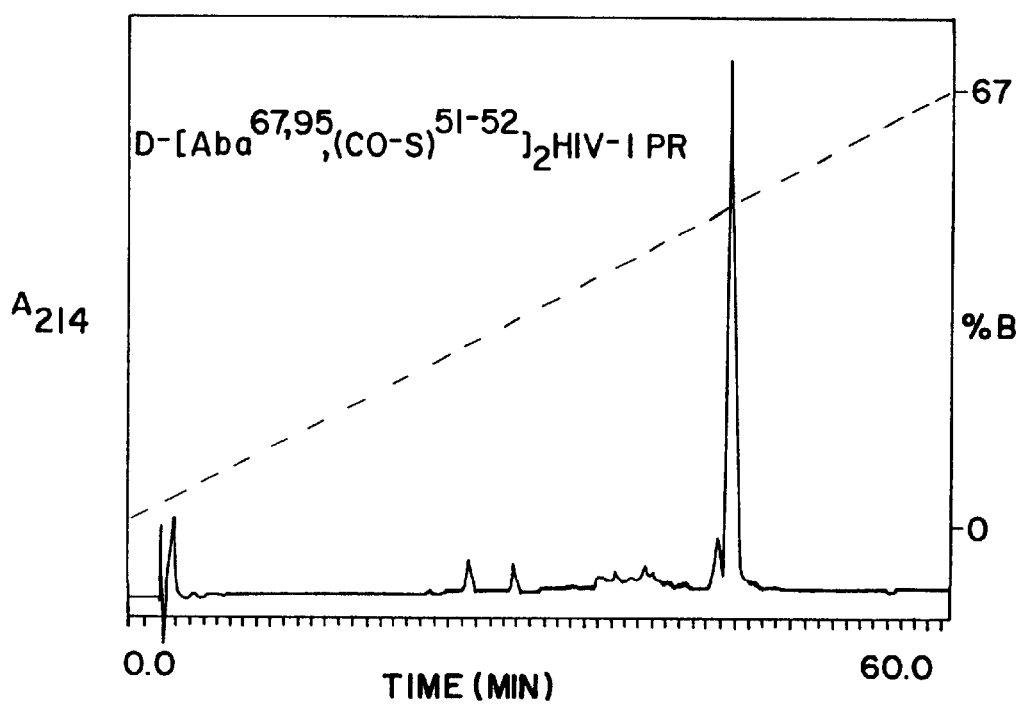
Figure 9C:
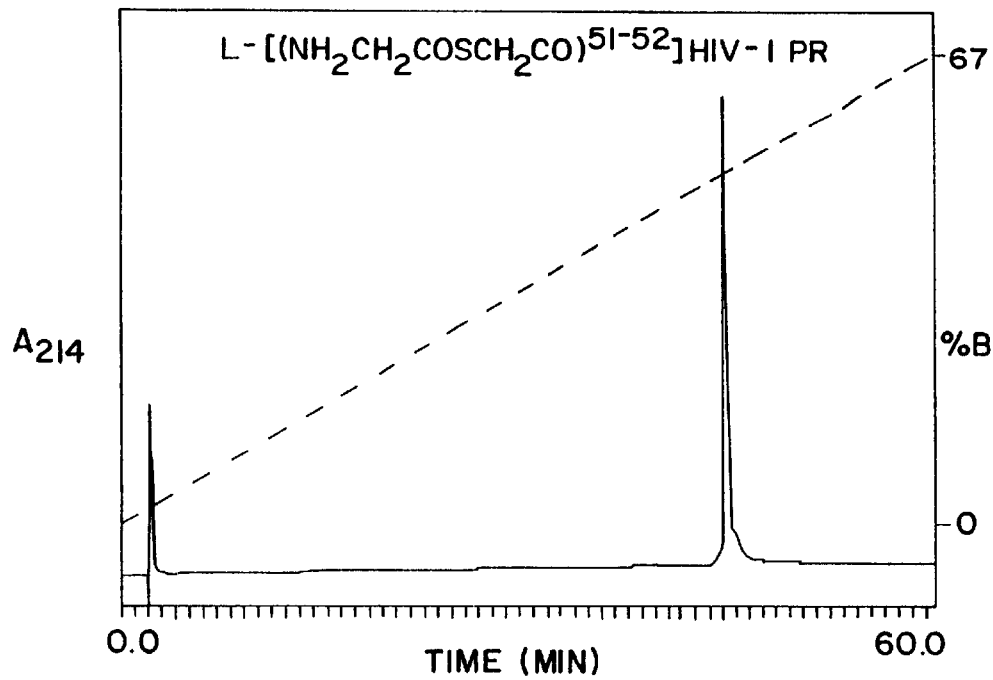
Figure 9D:
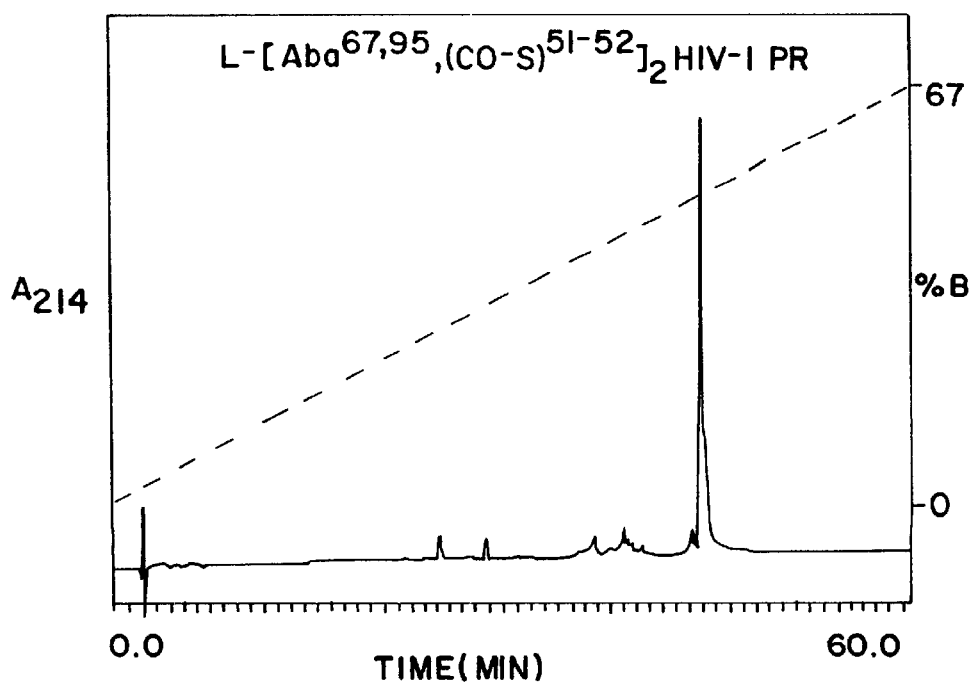

After preparative reverse phase HPLC purification (Vydac 218TP101550-5×25 cm, 0.1% TFA/CH$_3$CN & 30–50 ml/min) the functionalized peptide segments are reacted in the presence of 6M GuHCl (in 0.1M phosphate buffer, pH 5.3) for 48 hours to form the ligated D-and L-[(NHCH$^2$COSCH$_2$CO)$^{51\text{-}52}$]HIV-1 PR monomers. FIG. 6 illustrates a composite chromatogram showing the two purified functionalized unprotected segments and the final (48 hour) ligation reaction product (bold) run on a Vydac 218TP5415 column eluted with 0.1% TFA (buffer A) and 0.9% TFA/CH$_3$CN, 1:9 (buffer B), at a flow rate of 1 ml/min.

After purification by reverse phase HPLC, the products may be separately folded by dialysis in 25 millimolar phosphate buffer, pH 5.5, in the presence of a 10-fold excess of either D- or L-[MVT-101] inhibitor (Ac-Thr-Ile-Nle-ψ-[CH$_2$NH]-Nle-Gln-Arg.NH$_2$) (SEQ ID NO 1) to yield the homodimeric enzymes. (Miller et al., (1989) *Science* 246, 1149.) Step reaction yields for the synthesis of the D- and L-[Aba$^{67,95}$ (CO—S)$^{51-52}$]$_2$HIV-1 protease analogs are provided by FIG. 7.

Total yield with respect to the synthesis of the D-[Aba$^{67,95}$ (CO—S)$^{51-52}$]$_2$ HIV-1 protease analog was 48 milligrams or 3.0%.

Total yield with respect to the synthesis of the L-[Aba$^{67,95}$ (CO—S)$^{51-52}$]$_2$ HIV-1 protease analog was 47 milligrams or 2.5%.

6. Physical Characterization of the Ligation Products, D- and L-[Aba$^{67,95}$ (CO—S)$^{51-52}$]$_2$HIV-1 Protease Analogs Ion spray mass spectrometry of the HPLC purified ligated products is illustrated in FIG. 8. Ion spray mass spectrometry reveals single molecular species in each case with observed molecular masses of 10768.9±1.4 daltons (D-enantiomer) and 10769.4±0.9 daltons (L-enantiomer) [Calculated: 10763.9 daltons (monoisotopic) and 10770.8 daltons (average)]. Minor amounts of dehydration byproducts were also detected. The sequences of the monomers were also examined by a new protein ladder sequencing technique utilizing a one step laser desorption mass spectrometric readout. FIG. 8 (A & C) illustrate labelled peaks representing a single molecular species differing in the number of excess protons. The observed molecular masses of the ligated products is 10768.9±1.4 daltons (D-enantiomer) and 10769.4±0.9 daltons (L-enantiomer) [Calculated: 10763.9 daltons (monoisotopic) and 10770.8 daltons (average)]. FIGS. 8(B & D) illustrate reconstructed mass spectra in which the raw data shown in A & C has been reduced to a single charge state. All data points in A & C are included in the calculations and no mathematical filtering is performed. The mass regions from 10 to 11 kD are shown for clarity.

FIG. 9 illustrates the reverse phase HPLC measurements of D- & L-[Aba$^{67,95}$ (CO—S)$^{51-52}$] HIV-1 PR ligation products. The ligated products from 6M GuHCl reveal a single peak in each case. Panels A and C illustrate the purified ligated monomers in 6M GuHCl. Panels B and D illustrate the homodimeric enzymes folded in the presence of D- or L-CMVT-1013 inhibitor, respectively, in 25 millimolar sodium phosphate buffer, pH 5.5. Note that, after folding, a number of minor autolysis products are seen in both the D- and L-[Aba$^{67,95}$ (CO—S)$^{51-52}$]$_2$HIV-1 protease preparations. At approximately 27 minutes, minor proteolytic products of the MVT-101 inhibitor peptide are also seen. It would seem that even in the presence of a large excess of inhibitor, the enzyme is still subject to a minor degree of autolysis. The samples were run on a Vydac 218TP5415 column eluted with 0.1% TFA (buffer A) and 0.9% TFA/CH$_3$CN, 1:9 (buffer B), at flow rate of 1 ml/min.

Figure 10A:
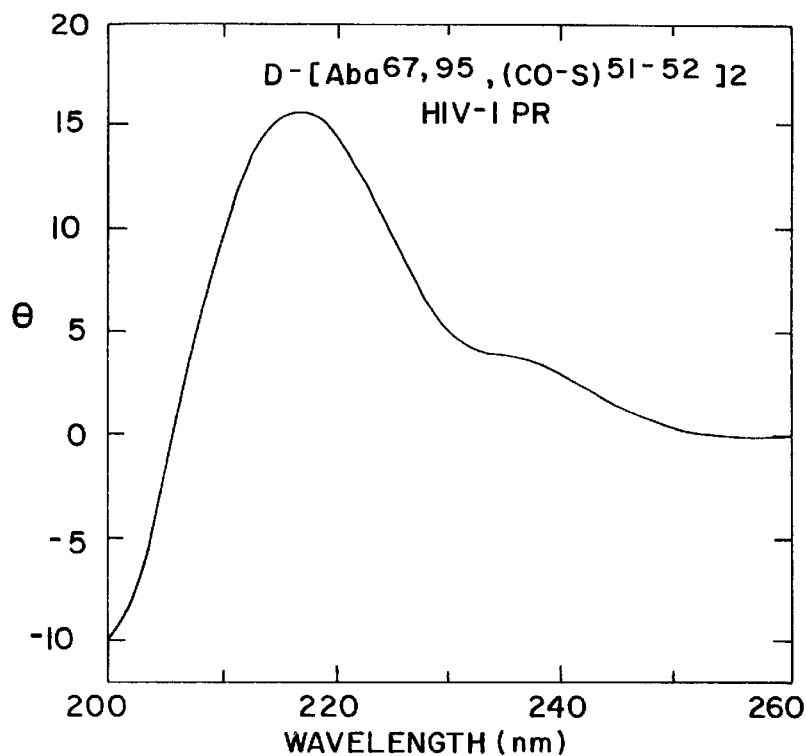
FIGS. 10A and 10B illustrate the far-ultraviolet circular dichroism spectrum of the D- and L-[Aba$^{67,\ 95}$ (CO—S)$^{51-52}$]$_2$HIV-1 protease analogs.
Figure 10B:
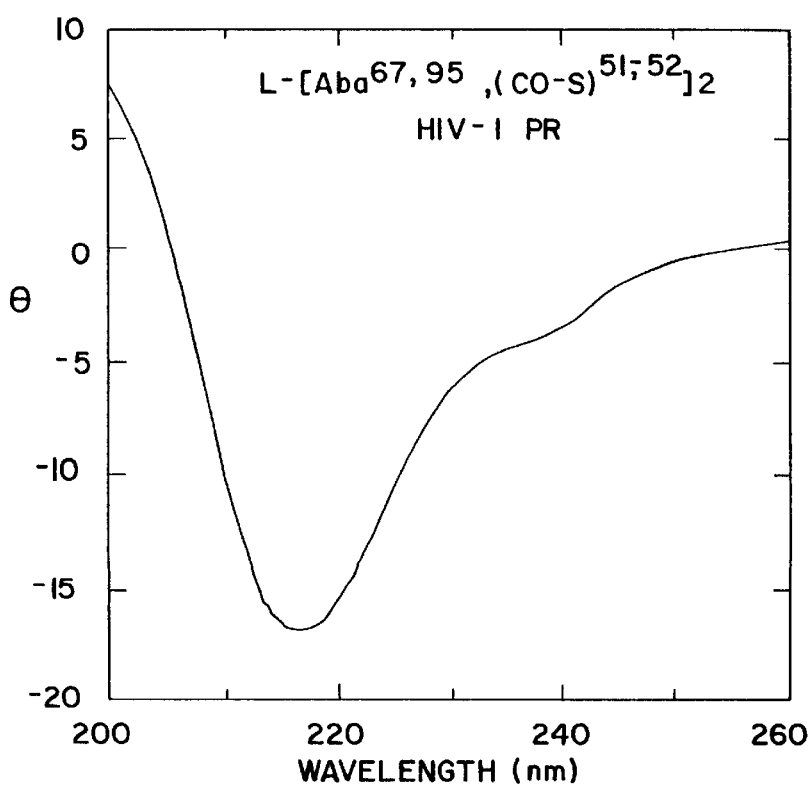

FIG. 10 illustrates the far-ultraviolet circular dichroism spectra of the folded D- and L-protease preparations. The spectra were recorded in 25 millimolar sodium phosphate buffer, pH 5.5 (0.4 mg/ml protease in the presence of inhibitor) at 25° C. in a quartz cell with a pathlength of 1 millimeter. Each preparation is of equal magnitude, but opposite sign, as expected for mirror image proteins. (Corigliano-Murphy et al., (1985) *Int. J. Peptide Protein Res.* 25, 225; and Zawadzke et al., (1992) *J. Am. Chem. Soc.* 114, 4002).

Figure 11:
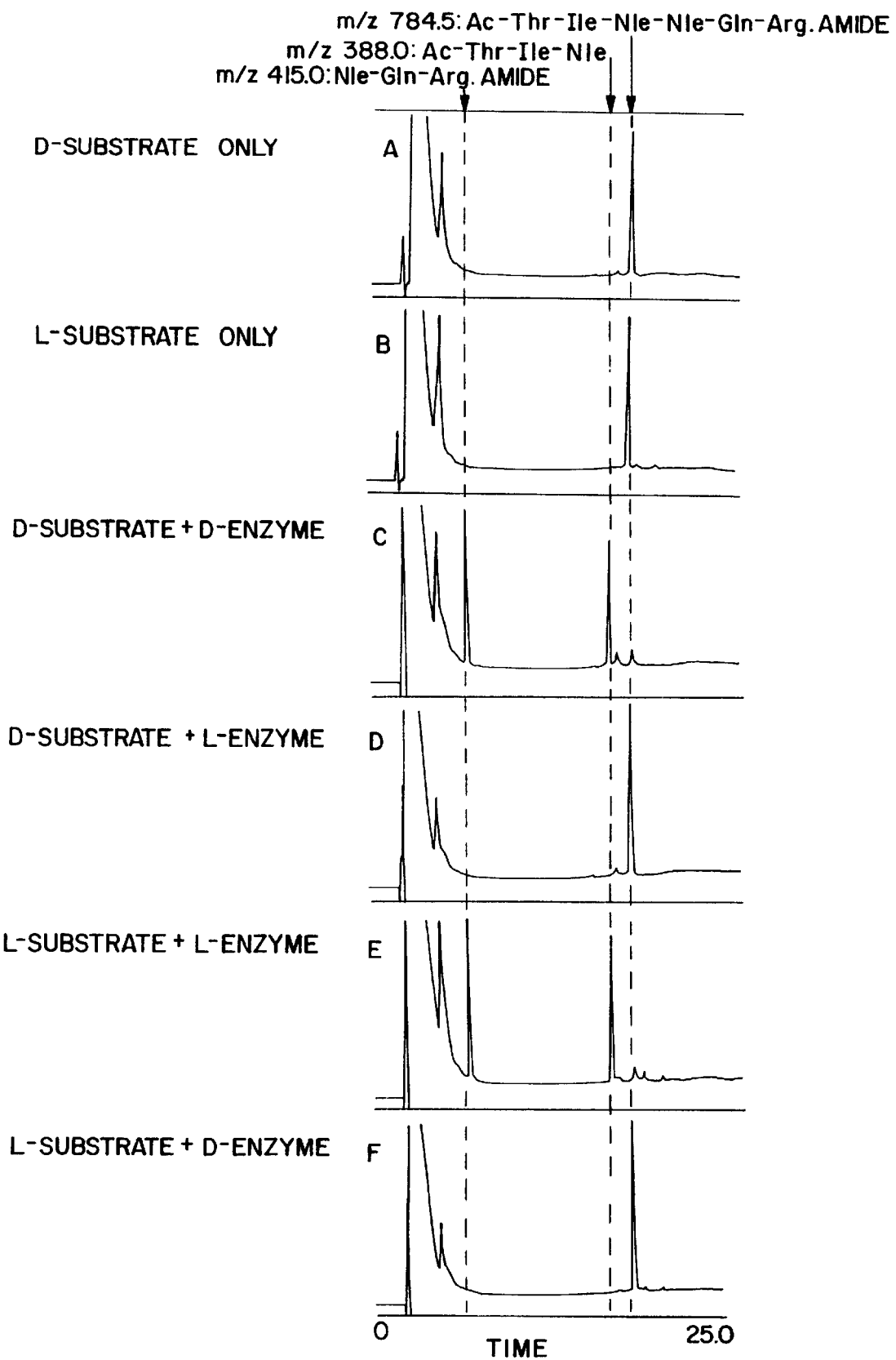
FIG. 11 illustrates the enzymatic activity of the [Aba$^{67,95}$, (CO—S)$^{51-52}$]$_2$ HIV-1 PR enantiomers on D- and L-isomers of the substrate Ac-Thr-Ile-Nle-Nle-Gln-Arg.amide.

7. Characterization of the Enzymatic Activity of Ligation Products, D- and L-[Aba$^{67,95}$ (CO—S)$^{51-52}$]$_2$ HIV-1 Protease Analogs FIG. 11 illustrates the enzymatic activity of the D- & L-[Aba$^{67,95}$ (CO—S)$^{51-52}$]$_2$ HIV-1 PR enantiomers may be determined by their action on D- and L-isomers of the hexapeptide substrate Ac-Thr-Ile-Nle-Nle-Gln-Arg.amide (an analog of the p24/p15 GAG viral processing site). The D-enzyme cleaves only the D-substrate and is inactive on the L-substrate, while the L-enzyme shows full activity towards the L-substrate, but is inactive towards the D-substrate. This reciprocal chiral specificity is also evident in the effect of chiral inhibitors. As shown in the Table, D-and L-[MVT-101] inhibits the cleavage of chiral fluorogenic substrates by the D- and L-HIV-1 PR analogues respectively, but has no effect on the action of the opposite enantiomer. Interestingly, the achiral inhibitor, Evans Blue, which shows mixed inhibition kinetics, inhibits both enantiomers of the enzyme.

TABLE

Chiral inhibitors show reciprocal chiral specificity against D- and L-[Aba$^{67,95}$(CO—S)$^{51-52}$]$_2$ HIV-1 PR*

|  | L-MVT101 | D-MVT101 | Evans Blue |
|---|---|---|---|
| D-[Aba$^{67,95}$(CO—S)$^{51-52}$]$_2$ HIV-1 PR | + | − | + |
| L-[Aba$^{67,95}$(CO—S)$^{51-52}$]$_2$ HIV-1 PR | − | + | + |

The D- and L-enzymes were separately assayed by the fluorogenic assay method using the corresponding chiral substrate, in the presence of 5×1C$_{50}$ concentration of inhibitor. The fluorogenic assays were performed with 15 ul aliquots (corresponding to 1.75 (±10%) mg protein) of each enzyme enantiomer in 100 millimolar MES buffer pH 6.5 added to a solution of 50 mM D- or L-fluorogenic substrate in the MES buffer. The substrate sequence was 2-aminobenzoyl-Thr-Ile-Nle-Phe(p-NO$_2$)-Gln-Arg amide (SEQ ID NO 2): it was synthesized with either D- or L-amino acid derivatives to provide the appropriate enantiomeric forms. The inhibitor Evans Blue is a non-peptide, achiral mixed competitive-uncompetitive inhibitor of the HIV-1 PR enzyme.

The enzymatic activity of the [Aba$^{67,95}$, (CO—S)$^{51-52}$]$_2$ HIV-1 PR enantiomers with respect to the D- and L-isomers of the substrate Ac-Thr-Ile-Nle-Nle-Gln-Arg.amide (SEQ ID NO 3) may be measured as follows. The substrate (1 mg/ml) is treated with enzyme (0.1 mg/ml) at pH 6.5 (MES buffer, 100 mM) for 30 minutes at 37° C. An aliquot of the reaction mixture is then chromatographed (Vydac 218TP5415 RP HPLC column) with a linear gradient, 0–40%, of buffer B (0.09% TFA/CH$_3$CN, 1:9) in buffer A (0.1% TFA) over 20 minutes (flow rate 1 ml/min, A$^{214nm}$). The peptide products are identified by ion spray MS as (H)-Nle-Gln-Arg.amide (m/z: 415.0—early eluting) and Ac-Thr-Ile-Nle-(OH) (m/z: 388.0—late eluting). Minor impurities present in the substrate preparations due to unpurified peptides are not cleaved. Panel A illustrates D-substrate only; panel B illustrates L-substrate only; panel C illustrates D-substrate plus D-enzyme; panel D illustrates D-substrate plus L-enzyme; panel E illustrates L-substrate and L-enzyme; panel F illustrates L-substrate plus D-enzyme.

8. Discussion of Examples 4–7

The HIV-1 protease enzyme exists as a homodimeric structure. It is a highly specific enzyme and this specificity and its catalytic activity depend on a precise 3-D structure being formed between the folded dimer and six residues of the substrate molecule.

The observed reciprocal specificities, therefore, show that the folded forms of the D- and L-enzyme molecules are mirror images of each other in all elements of the 3-D structure responsible for their enzymatic activity. This is consistent with their observed CD spectra.

The 3-D structure of a folded enzyme molecule contains numerous chiral elements in secondary and supersecondary structure, in tertiary structure and in quarterny structure, as illustrated in FIG. 3.

Since the only difference between the synthetic D and L-polypeptide chains is the stereochemistry of the a-carbon atoms (and the CB atoms of Ile and Thr) of the amino acids, it is concluded that the stereochemistry of the backbone determines all aspects of higher structure in this protein.

The observations of reciprocal chiral specificity in the enzymatic activity of the D- and 1-HIV-1 proteases disclosed herein, serve to generalize and emphasize the chiral nature of the biochemical interactions of proteins. The large amounts of high purity D- and L-enzyme enantiomorphs prepared using the chemical ligation method will allow a thorough experimental evaluation of the use of D-, L-proteins in X-ray crystallography.

The foregoing is intended as illustrative of the present invention but not limiting. Numerous variations and modifications can be effected without departing from the true spirit and scope of the invention.

---

What is claimed is:

1. A method for screening a library for identifying an active enantiomer of a chiral drug candidate having activity with respect to an L-enzyme, the activity being selected from a group consisting of enzyme inhibition and enzyme binding, the chiral drug candidate having a first and a second enantiomer, the first enantiomer being active and the second enantiomer being inactive with respect to the L-enzyme, the library including the second enatiomer but excluding the first enatiomer, the method comprising the following steps:

Step A: providing a D-enzyme, the D-enzyme being an enantiomer of the L-enzyme, the second enantiomer of the chiral drug candidate being active with respect to the D-enzymne; then Step B: contacting the library under reaction conditions with the D-enzyme of said Step A for identifying the second enatiomer by its activity with the D-enzyme; then Step C: providing the first enatiomer using information obtained from the identification of the second enatiomer in said Step B; and then Step D: contacting the L-enzyme under reaction conditions with the first enantiomer, provided in said Step C, for verifying the activity of the first enantiomer of the chiral drug candidate with rspect to the L-enzyme.

2. A method as described in claim 1 wherein the L-enzyme includes a receptor or binding site.

* * * * *

UNITED STATES PATENT AND TRADEMARK OFFICE
CERTIFICATE OF CORRECTION

PATENT NO. : 6,040,133
DATED : March 21, 2000
INVENTOR(S) : Stephen Brian Henry Kent, Saskia Charlotte Florence Milton and Raymond Cecil deLisle Milton It is certified that error appears in the above-identified patent and that said Letters Patent is hereby corrected as shown below:

Title page,
Item [60], Related U.S. Application Data, should read as follows:
-- Division of application Ser. No. 08/343,585, Dec. 2, 1994 which is a national phase of application No. PCT/US93/05441, filed Jun. 7, 1993 which is a continuation-in-part of application Ser. No. 07/894,817, filed Jun. 5, 1992, now abandoned, whose disclosures are incorporated herein by reference. --

Column 1,
Line 4, should read as follows:
-- This application is a division of application Ser. No. 08/343,585, filed Dec. 2, 1994 which is a national phase of application No. PCT/US93/05441, filed Jun. 7, 1993 which is a continuation-in-part of application Ser. No. 07/894,817, filed Jun. 5, 1992, now abandoned, whose disclosures are incorporated herein by reference. --

Signed and Sealed this

Twenty-sixth Day of August, 2003

JAMES E. ROGAN
*Director of the United States Patent and Trademark Office*

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 6 amino acids
          (B) TYPE: amino acid
          (D) TOPOLOGY: linear (ii) MOLECULE TYPE: peptide (v) FRAGMENT TYPE: internal (ix) FEATURE:
          (A) NAME/KEY: Modified-site
          (B) LOCATION: 1
          (D) OTHER INFORMATION: /label= N-acetyl
               /note= "An N-acetyl group is located at the amino
               terminus of the peptide."

(ix) FEATURE:
          (A) NAME/KEY: Modified-site
          (B) LOCATION: 3
          (D) OTHER INFORMATION: /label= Nle
               /note= "The modified amino acid, Nle, is present
               at this position."

(ix) FEATURE:
          (A) NAME/KEY: Modified-site
          (B) LOCATION: 4
          (D) OTHER INFORMATION: /label= Nle
               /note= "The modified amino acid, Nle, is present
               at this position."

(ix) FEATURE:
          (A) NAME/KEY: Modified-site
          (B) LOCATION: 3..4
          (D) OTHER INFORMATION: /label= psiCH2NH
               /note= "The scissile peptide bond between these
               amino acids has been replaced by a reduced analog,
               psiCH2NH."

(ix) FEATURE:
          (A) NAME/KEY: Modified-site
          (B) LOCATION: 6
          (D) OTHER INFORMATION: /label= Amide
               /note= "An amide is located at the carboxy
               terminus of the peptide."

(xi) SEQUENCE DESCRIPTION: SEQ ID NO:1:

Thr Ile Xaa Xaa Gln Arg
1               5
```

(2) INFORMATION FOR SEQ ID NO:2:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /note= "A 2-aminobenzoyl group is
            located at the amino terminus of the peptide."

(ix) FEATURE:
        (A) NAME/KEY: Modified-site
        (B) LOCATION: 3
        (D) OTHER INFORMATION: /label= Nle
            /note= "The modified amino acid, Nle, is present
            at this position."

(ix) FEATURE:
        (A) NAME/KEY: Modified-site
        (B) LOCATION: 4
        (D) OTHER INFORMATION: /label= Phe-pNO2
            /note= "The modified amino acid, Phe-pNO2, is
            present at this position."

(ix) FEATURE:
        (A) NAME/KEY: Modified-site
        (B) LOCATION: 6
        (D) OTHER INFORMATION: /label= Amide
            /note= "An amide is located at the carboxy
            terminus of the peptide."

(xi) SEQUENCE DESCRIPTION: SEQ ID NO:2:

Thr Ile Xaa Xaa Gln Arg
1             5

(2) INFORMATION FOR SEQ ID NO:3:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 1
        (D) OTHER INFORMATION: /label= Ac
            /note= "An acetyl, Ac, group is located at the
            amino terminus of the peptide."

(ix) FEATURE:
        (A) NAME/KEY: Modified-site
        (B) LOCATION: 3
        (D) OTHER INFORMATION: /label= Nle
            /note= "A modified amino acid, Nle, is located at
            this position."

(ix) FEATURE:
        (A) NAME/KEY: Modified-site
        (B) LOCATION: 4
        (D) OTHER INFORMATION: /label= Nle
            /note= "A modified amino acid, Nle, is located at
            this position."

(ix) FEATURE:
        (A) NAME/KEY: Modified-site

```
            (B) LOCATION: 6
            (D) OTHER INFORMATION: /label= Amide
                /note= "An amide is located at the carboxy
                   terminus of the peptide."

(xi) SEQUENCE DESCRIPTION: SEQ ID NO:3:

Thr Ile Xaa Xaa Gln Arg
1               5
```